United States Patent
Terman

(10) Patent No.: US 10,952,975 B2
(45) Date of Patent: Mar. 23, 2021

(54) COMPOSITIONS AND METHODS FOR TREATMENT OF CANCER

(71) Applicant: David S Terman, Pebble Beach, CA (US)

(72) Inventor: David S Terman, Pebble Beach, CA (US)

( * ) Notice: Subject to any disclaimer, the term of this patent is extended or adjusted under 35 U.S.C. 154(b) by 0 days.

(21) Appl. No.: 16/817,268

(22) Filed: Mar. 12, 2020

(65) Prior Publication Data

US 2020/0297658 A1    Sep. 24, 2020

Related U.S. Application Data

(60) Provisional application No. 62/820,747, filed on Mar. 19, 2019.

(51) Int. Cl.
| | | |
|---|---|---|
| A61K 31/09 | (2006.01) | |
| A61K 35/18 | (2015.01) | |
| A61K 9/00 | (2006.01) | |
| A61K 38/42 | (2006.01) | |
| A61K 45/06 | (2006.01) | |

(52) U.S. Cl.
CPC ............ *A61K 31/09* (2013.01); *A61K 9/0019* (2013.01); *A61K 35/18* (2013.01); *A61K 38/42* (2013.01); *A61K 45/06* (2013.01)

(58) Field of Classification Search
CPC ........ A61K 31/09; A61K 38/42; A61K 35/18; A61K 9/0019; A61K 45/06
See application file for complete search history.

(56) References Cited

U.S. PATENT DOCUMENTS

2012/0195869 A1* 8/2012 Terman .................. A61P 35/00
424/93.73

OTHER PUBLICATIONS

Sun et al., Exogenous sickle erythrocytes combined with vascular disruption trigger disseminated tumor vaso-occlusion and lung tumor regression. JCI Insight, vol. 4, No. 7 (online Feb. 19, 2019) e125535. (Year: 2019).*
Tozer GM et al. Disrupting tumour blood vessels Nat Rev Cancer 5:423-35. (2005).
Mita MM et al Vascular-disrupting agents in oncology Expert Opinion on Investigational Drugs 22: 317-328 (2013).
Gaya AM et al Vascular disrupting agents: a new class of drug in cancer therapy. Clin Oncol (R Coll Radiol). 7::277-90.(2005).
Cha HJ et al. Evolutionarily Repurposed Networks Reveal the Well-Known Antifungal Drug Thiabendazole to Be a Novel Vascular Disrupting Agent PLoS Biol 10(8): e1001379. doi:10.1371/journal.pbio.1001379 (2012).
Mason, RP, Zhao D, Liu L, Trawick ML, Pinney KG a Perspective on Vascular Disrupting Agents that Interact with Tubulin: Preclinical Tumor Imaging and Biological Assessment Integr Biol (Camb). Apr. 1, 2011; 3(4): 375-387. doi:10.1039/c0ib00135j).

* cited by examiner

*Primary Examiner* — Kara D Johnson

(57) ABSTRACT

Resistance of randomly dispersed and oxygen-starved lung tumor cells to chemo- and radiotherapy constitutes the vast majority recurrences and death from lung cancer. We use sickle cells derived from humans with sickle cell anemia to target oxygen-deprived tumor cells that persist and multiply after conventional treatment. Transfused sickle cells selectively occluded tumor microvessels and shut down blood flow to these oxygen-deprived pockets leading to tumor cell death and complete shrinkage of aggressive lung tumors. Combining the sickle cells with a vascular disrupting agents and radiation injure and narrow tumor blood vessels, amplified the scale of sickle cell-induced blood vessel closure and tumor cell killing. The strength of the tumor killing produced by this combination exceeded that of either agent alone or combined with conventional anti-angiogenics, chemotherapy or radiation. Combinatorial sickle cells-Combretastatin treatment thereby constitutes a major advance toward eradicating treatment-resistant tumor cells and reducing the frequency of lung cancer recurrence.

9 Claims, 11 Drawing Sheets

COMPOSITIONS AND METHODS FOR TREATMENT OF CANCER

CROSS REFERENCE TO RELATED DOCUMENTS

Figure 1:
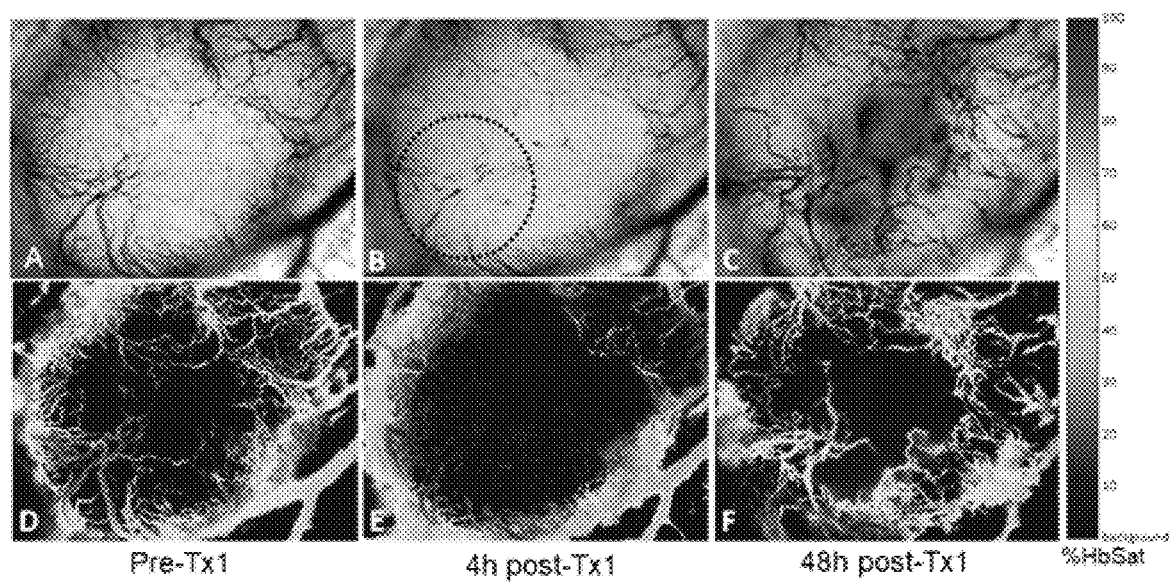

The instant application claims priority to U.S. provisional patent application Ser. No. 62/820,747 filed on Mar. 16, 2019. Provisional application Ser. No. 62/820,747 is incorporated in entirety by reference with its references. All references cited in the instant application and their references are incorporated in entirety by reference.

BACKGROUND OF THE INVENTION

Hypoxic tumor niches and their underlying molecular axes have been a chief targets of molecular cancer therapeutics. Of paramount concern to investigators is that such niches are associated with resistance to conventional cancer treatment and their persistence is a major cause of tumor recurrence (Wilson W R, Hay M P. Nat Rev Cancer. 2011; 11(6):393-410). Under hypoxic conditions within tumors, conserved oxygen sensors activate hypoxia-inducible transcription factors and pro-angiogenic signals (Kerbel R S. N Engl J Med. 2008; 358(19):2039-2049.). The latter induce a disordered network of blood vessels resulting in cyclic or chronic deoxygenation (Pries A R, Nat Rev Cancer. 2010; 10(8):587-593). As tumor growth outscales neoangiogenesis, tumor cells rendered chronically hypoxic may survive, proliferate and become treatment resistant (Brunelle J K, Chandel N S, g Drug Resist Updat. 2010; 13(1-2):16-28).

The failure of conventional treatment has prompted a universal search for conceptually new tools and strategies to eradicate these treatment-resistant hypoxic tumor cell subpopulations. Anti-angiogenic agents that limit the tumor blood supply to these niches by targeting receptors on embryonic blood vessels usually lead to tumor regrowth by activation of alternate synthetic pathways, hypoxia inducible factors or tumor cells that evade the effect of therapy (Abdollahi A, Folkman J Drug Resist Updat. 2010; 13(1-2):16-28). Likewise, polymeric nanocarriers occlude only a fraction of mature tumor blood vessels and in the absence of hypoxia sensing systems fail to access oxygen deprived regions (Vasuri F, et al. World J Gastroenterol. 2014; 20(37): 13538-13545). We therefore turned to the sickle erythrocyte (SSRBC) derived from a mutated erythroid lineage. These cells circulate freely and possess a unique hypoxia-sensing functionality which becomes operative under severely hypoxic conditions in low velocity microvessels (Manwani D, Frenette P S Blood. 2013; 122(24):3892-3898). SSRBCs are trapped in these vessels leading to HbS desaturation, polymerization and formation of tetrameric spicules rendering them rigid, adhesive and prone to vaso-occlusive aggregation (Ballas S K, Mohandas N. Microcirculation. 2004; 11(2):209-225). Intravital microscopy observations show that infused SSRBCs home to established tumor, form aggregates in tumor vessels and induce focal vessel closure. Together with pro-oxidants or oncogenic virus, SSRBCs also produce a therapeutic tumor growth delay but fail to produce complete tumor regressions (Terman D S, et al. PLoS One. 2013; 8(1):e52543).

In search of agents that could increase the efficiency and scale of SSRBC-mediated tumor killing, we turned to the vascular disruptant Combretastatin A4 (AVE8062 or CA-4). The latter is derived from the South African bush willow tree, Combretum caffrum. It binds to tumor endothelial β-tubulin subunits, inhibits microtubule formation and induces cytoskeletal alterations leading to vascular collapse, blood stasis, focal hypoxia, and ischemic tumor cell necrosis (Tozer G M et al., Nat Rev Cancer. 2005; 5(6):423-435). Despite these potent effects, CA-4 and its diphosphate derivative fail to eliminate viable tumor cells at the tumor rim resulting in rapid tumor regrowth (Siemann D W Cancer Treatment Rev. 2011; 37(1):63-74). Combining CA-4 with other therapeutics, such as radiation, cytotoxics, anti-angiogenics and biologics failed to the alleviate the peripheral tumor regrowth in murine tumor models (Siemann D W et al., Anticancer Res. 2008; 28(4B):2027-2031; Clémenson C et al., Crit Rev Oncol Hematol. 2013; 86(2):143-160)).

We hypothesized that CA-4's selective induction of tumor endothelial cell injury, blood stagnation, hypoxia could create a microvascular milieu wherein SSRBCs could efficiently deoxygenate, form microaggregates and induce a broad scale of tumor vessel closure and infarction. Such massive vaso-occlusion-infarction could not only encompass hypoxic niches, but also the treatment-resistant tumor rim. To this end, we introduce hypoxia-reactive SSRBCs as a new therapeutic whose physiologic adaptation to CA-4-induced tumor blood stasis and microvascular hypoxia results in an unprecedented scale of tumor microvessel closure and infarction that obliterates treatment-resistant hypoxic niches and the tumor rim. The SSRBCs-CA-4 regimen produced complete tumor regressions whereas each therapeutic alone or combined with conventional anti-angiogenics, cytotoxics or radiation resulted in tumor progression. Collectively, these findings provide conceptually new tools, mechanisms and strategies whereby drug-induced tumor endothelial remodeling licenses broad propagation of SSRBC-mediated vessel closure culminating in tumor eradication.

SUMMARY OF INVENTION

Hypoxic tumor niches are chief causes of treatment-resistance and tumor recurrence. Sickle erythrocytes' (SSRBCs') intrinsic oxygen-sensing functionality empowers them to access such hypoxic niches, wherein they form microaggregates, that induce focal vessel closure. In search of measures to augment the scale of SSRBC-mediated tumor vaso-occlusion, we turned to the vascular disruptant Combretastatin A-4 (CA-4). CA-4 induces selective tumor endothelial injury, blood stasis and hypoxia, but fails to eliminate peripheral tumor foci. Here we show that introduction of deoxygenated SSRBCs into tumor microvessels treated with CA-4 and sublethal radiation (SR) produces a massive surge of tumor vaso-occlusion and broadly propagated tumor infarctions that engulfs treatment-resistant hypoxic niches and eradicates established lung tumors. Tumor regression was corroborated by significant treatment effect histologically. Treated tumors displayed disseminated microvessels occluded by tightly-packed SSRBCs along with widely distributed pimidazole-positive-hypoxic tumor cells. Humanized HbS knockin mice (SSKI), but not in HbA knockin mice (AAKI) showed a similar treatment response underscoring SSRBCs as the paramount tumoricidal effectors. Thus, CA-4-SR-remodeled tumor vessels license SSRBCs to produce an unprecedented surge of tumor vaso-occlusion and infarction that envelops treatment-resistant tumor niches resulting in complete tumor regression. These innovative tools, strategically deployed, thereby constitute a major conceptual advance with compelling translational potential.

FIGURE LEGENDS

FIG. 1. Brightfield and corresponding hemoglobin saturation (HbSat) images of an established Caki-1 tumor before and after CA-4 administration. (A,D,G) Pretreatment images show original vascular structure with Hb saturation of <10% enveloping 38% of the tumor area. (B,E,G) Four hours after CA-4 administration, tumor vessels in the tumor exhibit vascular collapse (circle, compare B and A) associated with Hb saturation of <10% covering 64% of the tumor area (**p=<0.000002 compared to pre-treatment values). (C,F) Forty-eight hours after CA-4 administration core vessels show oxygenation recovery with Hb saturation <10% engulfing 24% of the tumor surface (*p=0.00005 and ***p=<0.000001 compared to pretreatment and 4-hour post treatment levels respectively, Student's t-test two-tailed). Images were obtained at ×2.5 magnification with image dimensions of 4.15×3.125 mm. The color scale shows % HbSat values. n=5 separate readings of Hb saturation <10% using the Image J software to determine % tumor area.

Figure 2:
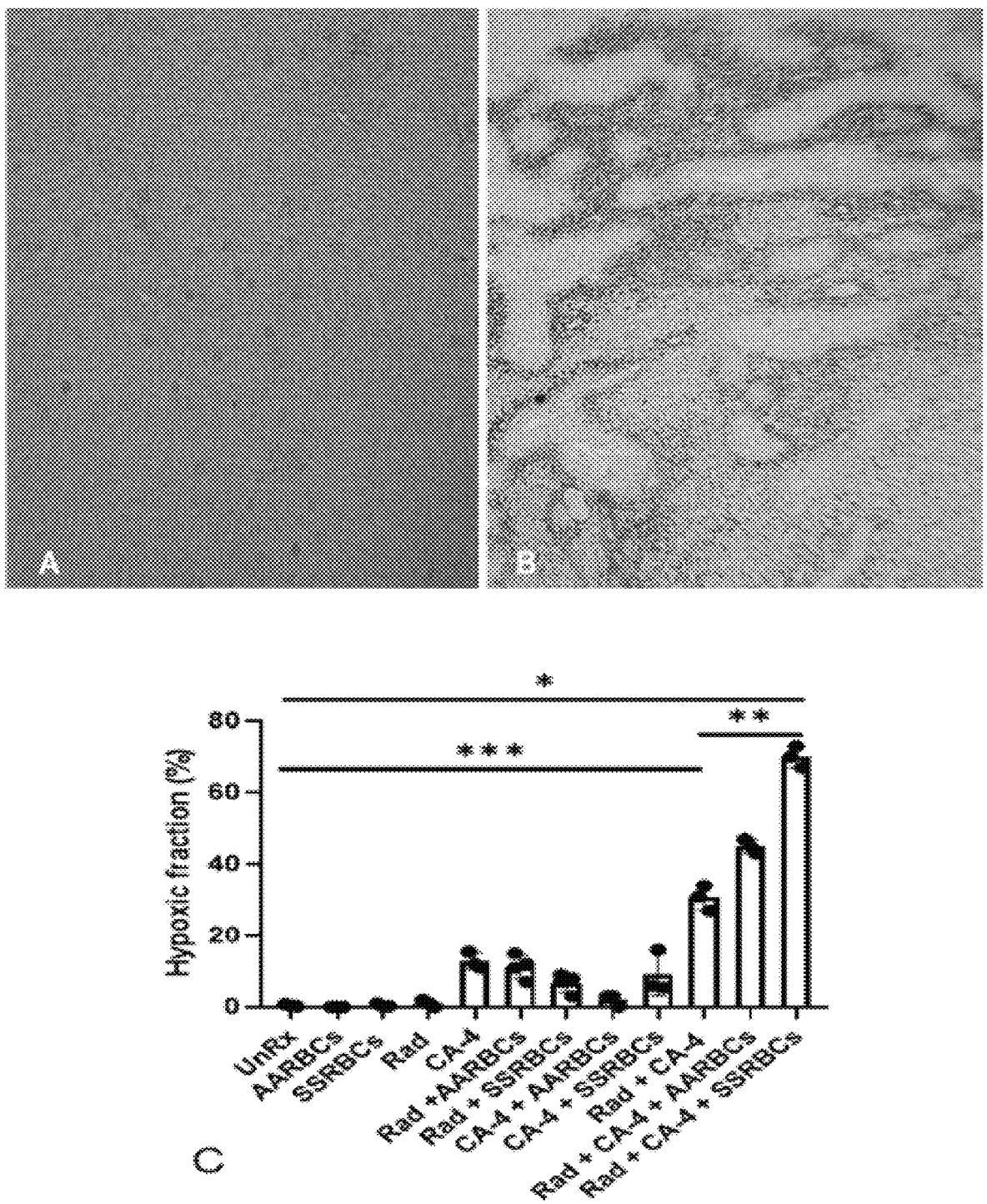

FIG. 2. Fractional uptake of pimidazole (hypoxic fraction) in sections of LLC in C57BL/6 mice obtained on day 14 after treatment with tumor SR (10 Gy) to the tumor on day 12 followed by CA-4 plus passive infusion of SSRBC or AARBC on day 13 as described in Methods. (A) Pimidazole uptake in LLC cells in untreated mice and (B) in mice treated with SSRBC-based triple therapy is shown. C) hypoxic fraction in tumor sections after treatment with SSRBC-based triple therapy exceeded that of AARBC-based triple therapy and the combination of sublethal radiation plus CA-4 treatment. (p≤0.0009). Hypoxic fraction of radiation plus CA-4 combined exceeded that of all other dual or single treatments (p=≤0.001). Hypoxic fraction in mice treated with SSRBC-based triple therapy also exceeded that of mice receiving all other treatments (*p≤0.0001, Student's t-test two-tailed), n=3. Diaminobenzidine (DAB, Scy Tek Laboratories, Logan, Utah) was used as the chromagen. The area showing pimidazole staining was determined using the Image-J software (NIH, Bethesda, Md.) and the analyses performed at ×10 magnification. Fractional area of pimidazole positivity was computed as a percentage of the total tumor area. Fraction of immunohistochemically hypoxic cells (IHF) was calculated as: $IHF = AF_{pim}/A_{total}$ where $AF_{pim}$ is the fraction showing pimonidazole staining and $A_{total}$ is the total tumor area.

Figure 3:
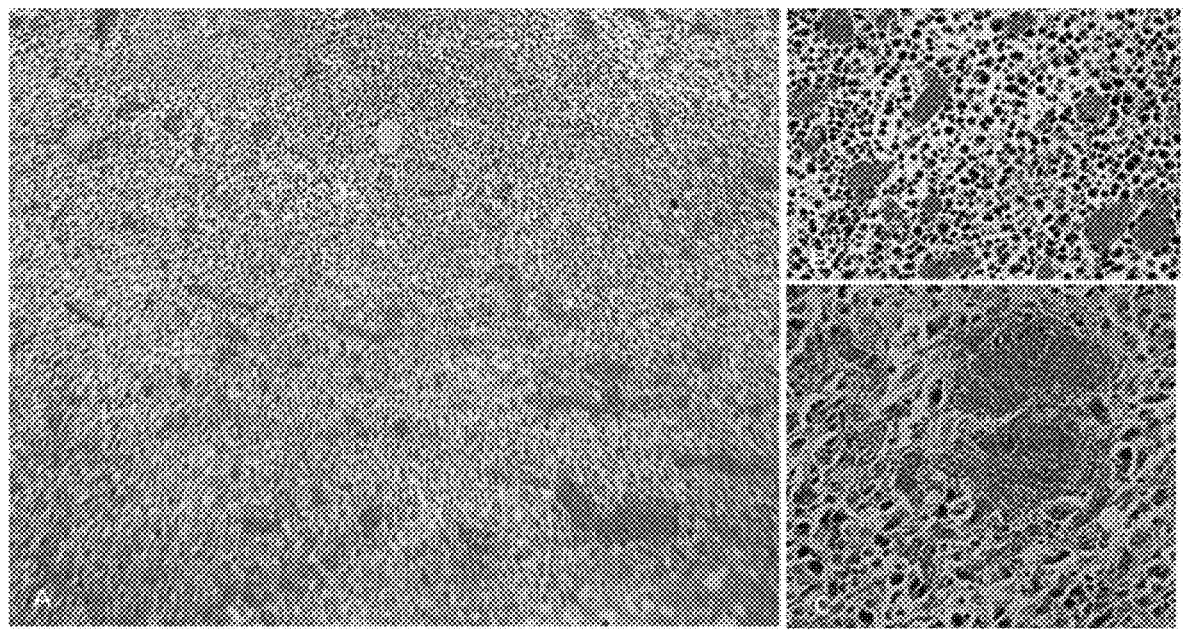
Figure 3:
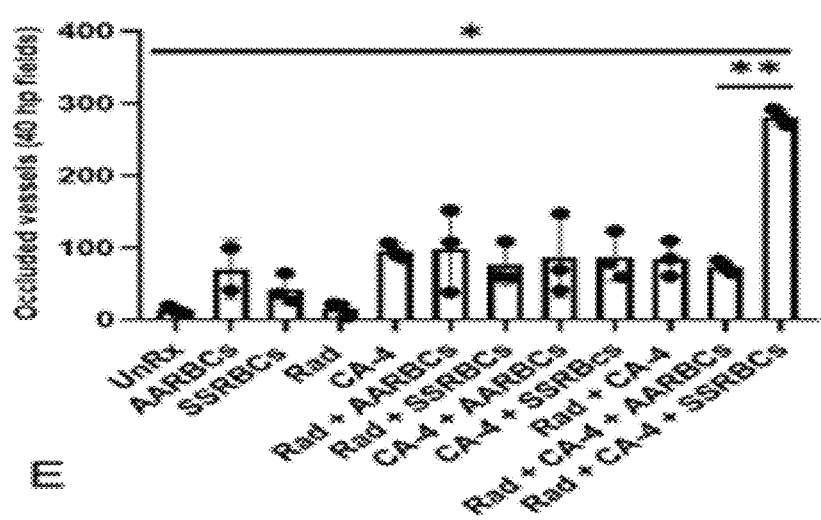

FIG. 3. Histopathology and quantitation of vaso-occlusion in sections of LLC in C57BL/6 mice obtained on day 14 after treatment with tumor SR (10 Gy) on day 12 followed by CA-4 plus passive infusion of SSRBC or AARBC on day 13 as described in Methods. Tumor sections from mice receiving SSRBC-based triple therapy shows (A) disseminated tumor vaso-occlusion, adjacent tumor cell necrosis and mononuclear cell infiltration (×10 mag.); (B) clustered tumor vessel occlusions surrounded by mononuclear cells (×25 mag.); (C) tumor vessels with tightly packed sickle cells (×40 mag.) (D) shows extensive vaso-occlusion with mononuclear cell infiltration engulfing the tumor periphery (×25 mag.). (E) demonstrates that the number of occluded tumor microvessels after treatment with SSRBC-based triple therapy exceeded that of similar AARBC-based triple therapy (**p=0.00009) and all dual and single treatments (*p≤0.0001, Student's t-test two-tailed). n=3. Tumor vaso-occlusion was quantitated in tumor sections by enumerating the total number of occluded microvessels in 40 fields at ×40 magnification. Microvessels were considered occluded when at least 80% of the vessel lumen was filled with erythrocytes.

Figure 4:
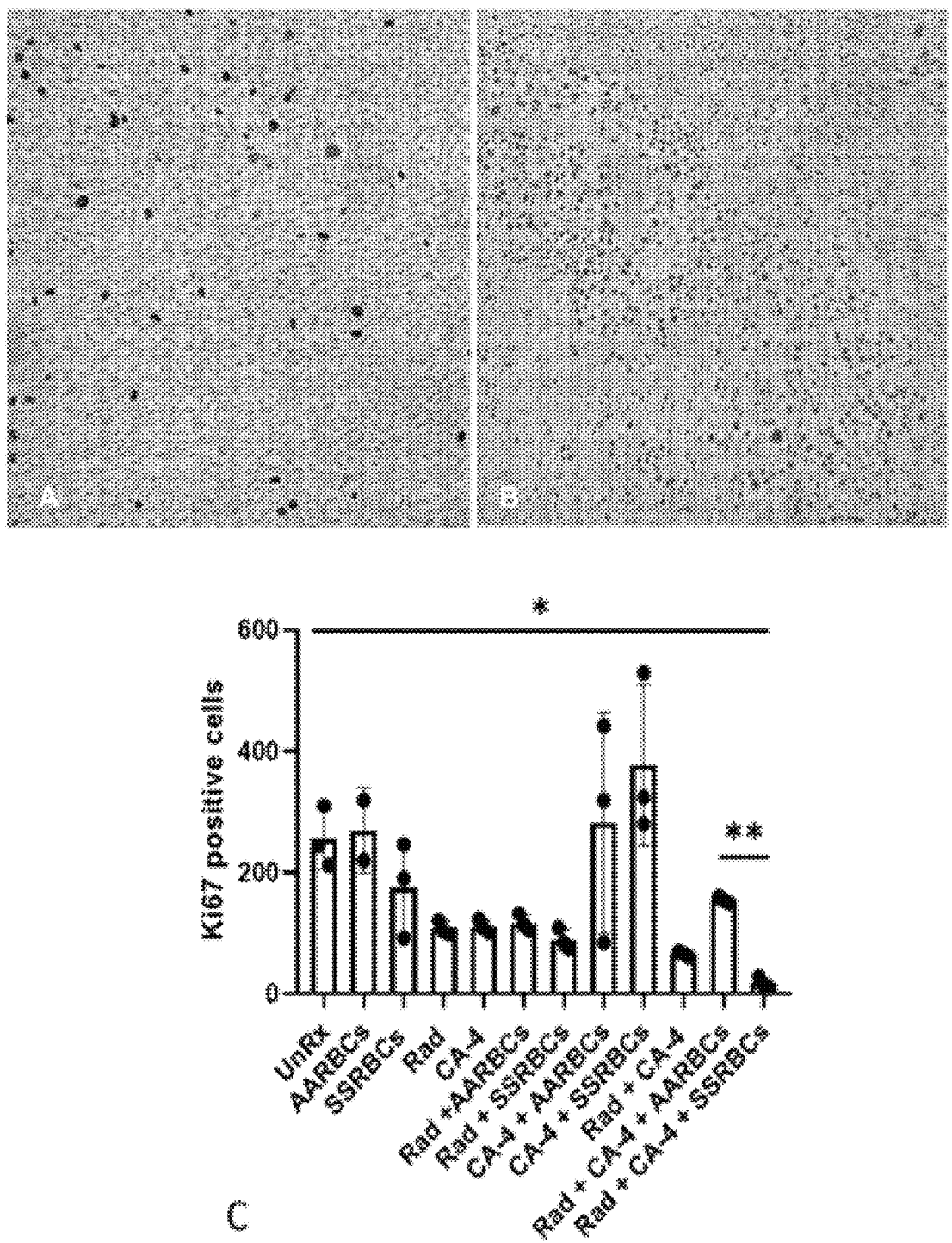

FIG. 4. Ki67 uptake in sections of LLC in C57BL/6 mice obtained on day 14 after treatment with tumor SR (10 Gy) on day 12 followed by CA-4 plus passive infusion of SSRBC or AARBC on day 13 as described in Methods. (A) Nuclear Ki67 uptake by LLC cells, an indicator of mitotically active tumor cells, from untreated mice and (B) in mice treated with SSRBC-based triple therapy is shown. (C) Ki67 uptake in tumor sections after one cycle of SSRBC-based triple therapy was diminished relative to that of AARBC-based triple therapy (**p≤0.0001, Student's t-test two-tailed) and all dual and single treatments (*p≤0.0001, n=3). Ki-67 immunopositive cells were quantitated tumor sections in 30 separate fields at ×40 magnification.

Figure 5:
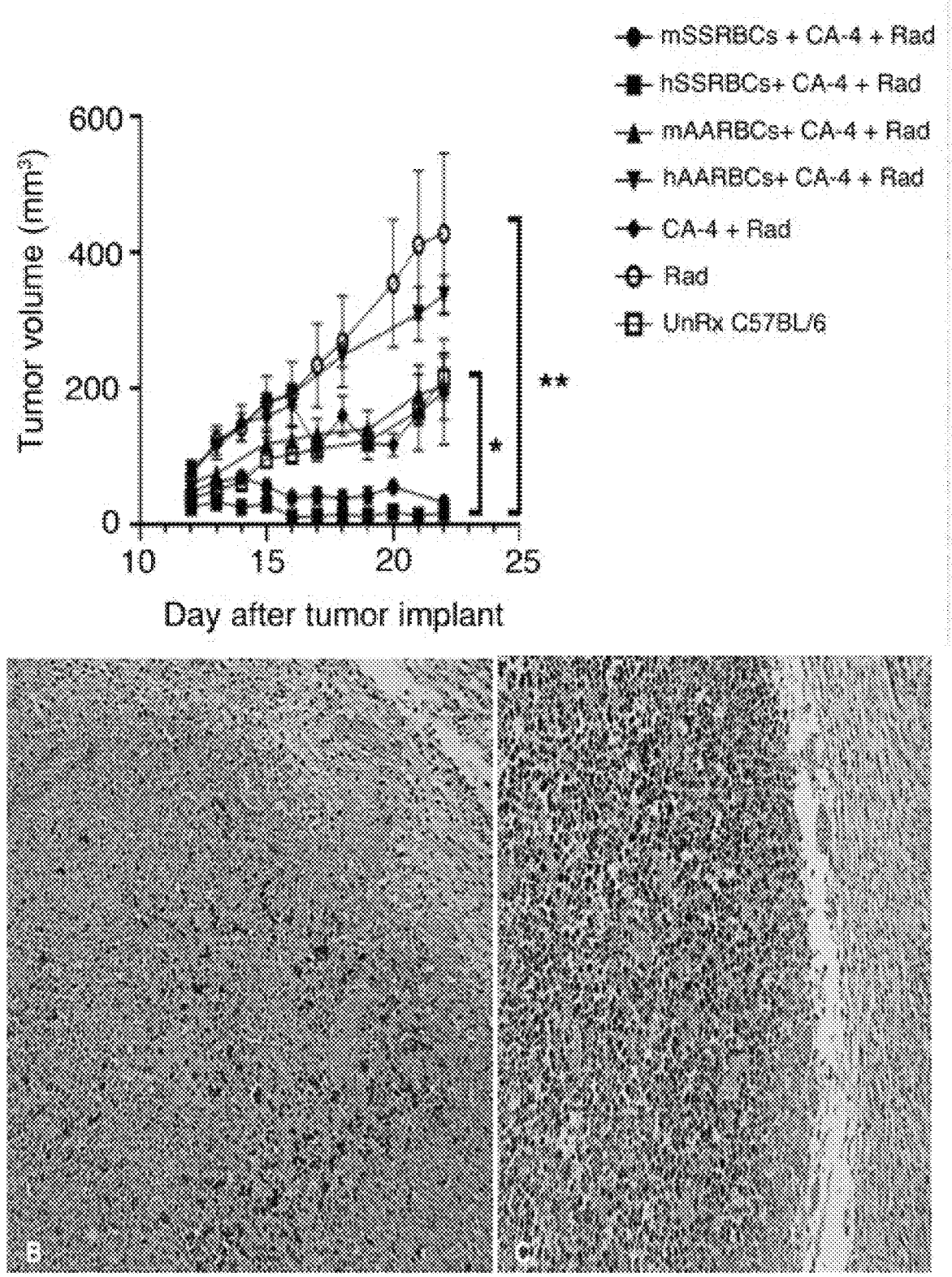

FIG. 5. Regression of established LLC in C57BL/6 mice obtained on day 22 after treatment with tumor SR (10 Gy) on day 12 followed by CA-4 plus passive infusion of human or mouse SSRBCs (triple therapy) on days 13,15 and 18 as described in Methods. (A) Tumor regression with human or mouse SSRBC-based triple agent therapy exceeded that of human AARBC-based triple agent therapy (*p=0.008), mouse AARBC-based triple therapy (*p=0.009), and all other dual and single treatments (**p≤0.009, Student's t-test two-tailed). n=6. (B,C) Histopathology of tumor sections obtained on day 22 from mice treated with SSRBC-based triple therapy shows extensive tumor vaso-occlusion and surrounding necrosis enveloping the tumor rim associated with mononuclear cell infiltration (×25 mag.).

Figure 6:
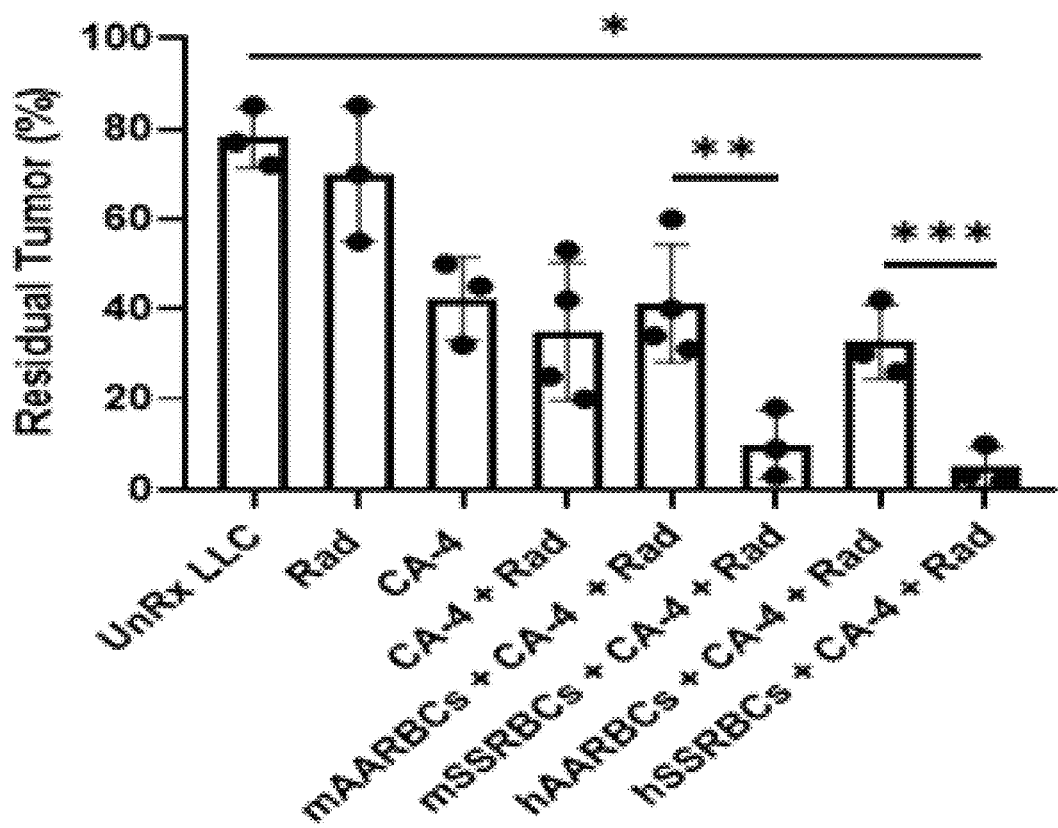

FIG. 6. Residual viable LLC in sections from mice bearing established LLC obtained on day 22 after treatment with tumor SR (10 Gy) on day 12 followed by CA-4 plus passive infusion of human or mouse SSRBCs (triple therapy) on days 13, 15 and 18 as described in Methods. Residual tumor in mice treated with mouse or human SSRBC-based triple agent therapy was significantly diminished relative to that of mice treated with mouse or human AARBC-based triple therapy (p=0.001 and *p=0.003 respectively). Residual tumor in mice treated with mouse or human SSRBC-based triple agent therapy was also significantly reduced relative to mice receiving dual or single treatments (*p≤0.0001, Student's t-test two-tailed). n=3-4.

Figure 7:
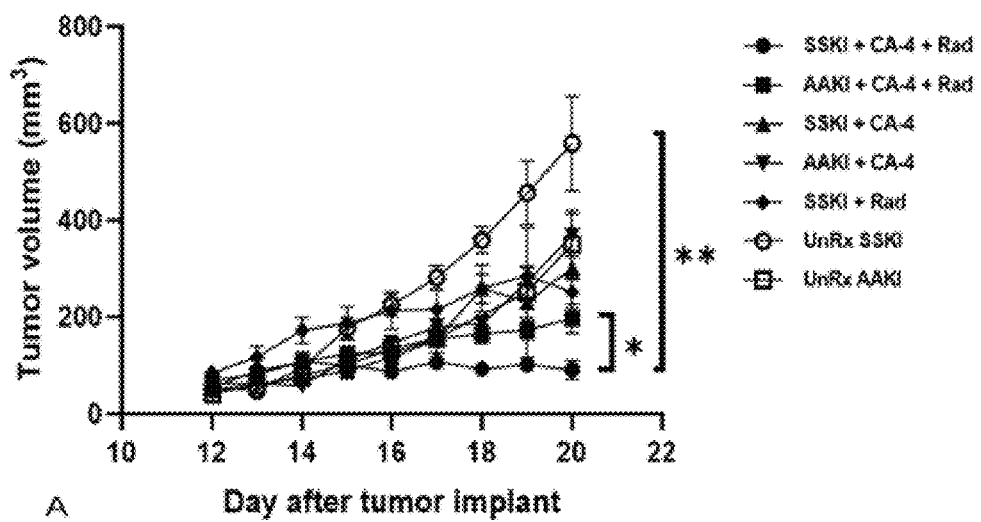
Figure 7:
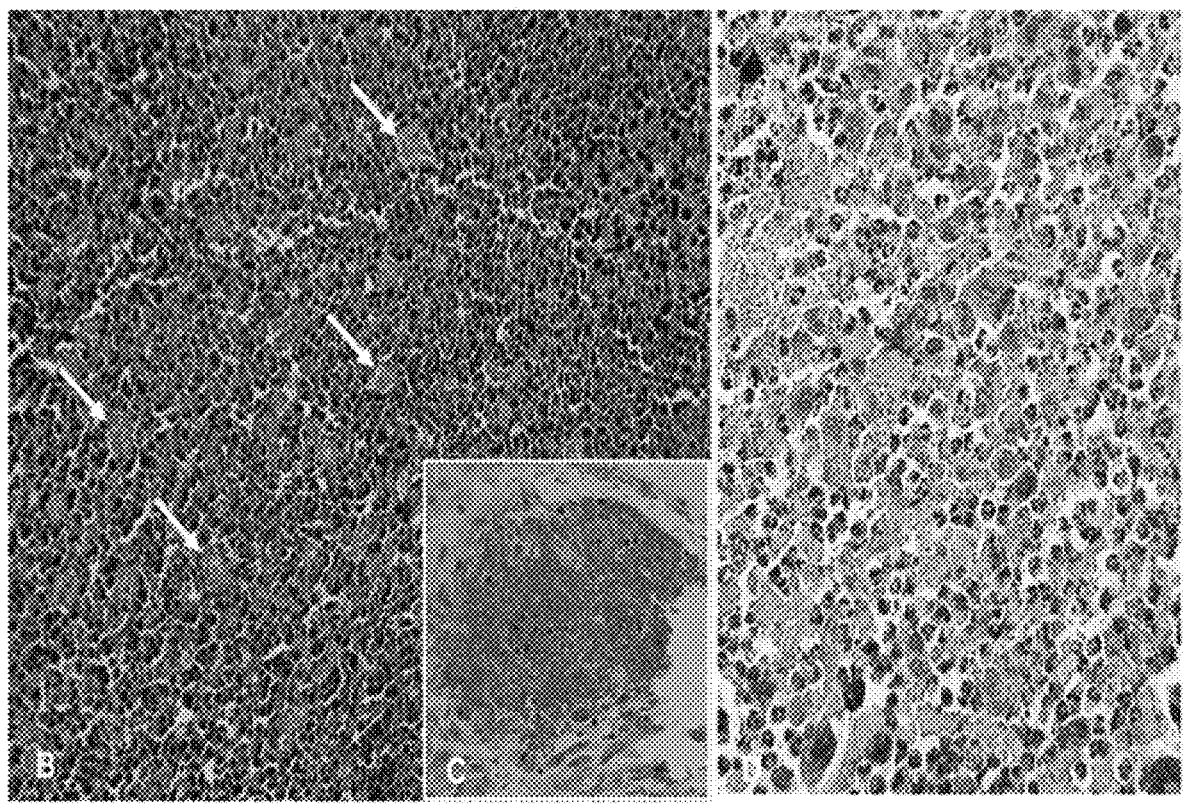

FIG. 7. Regression of established LLC in SSKI or AAKI mice obtained on day 20 after treatment with tumor SR (10 Gy) on day 12 followed by CA-4 on days 13, 15 and 18 as described in Methods. (A) Tumor regression in SSKI mice exceeded that of similar therapy in AAKI mice (*p=0.01) and all other dual and single treatments (**p≤0.008, Student's t-test two-tailed). n=6. (B) Histopathology of tumor sections obtained from SSKI mice at day 20 after treatment with SR (10 Gy) on day 12 followed by CA-4 on days 13, 15 and 18 shows extensive tumor vaso-occlusion (arrows) and infarction enveloping the core and tumor periphery (×25 mag.). (C) Representative tumor blood vessel occluded with tightly packed sickle cells (×40 mag.). (D) Tumor cell necrosis, mononuclear cell infiltrate adjacent to occluded blood vessels is shown (×40× mag.).

Figure 8:
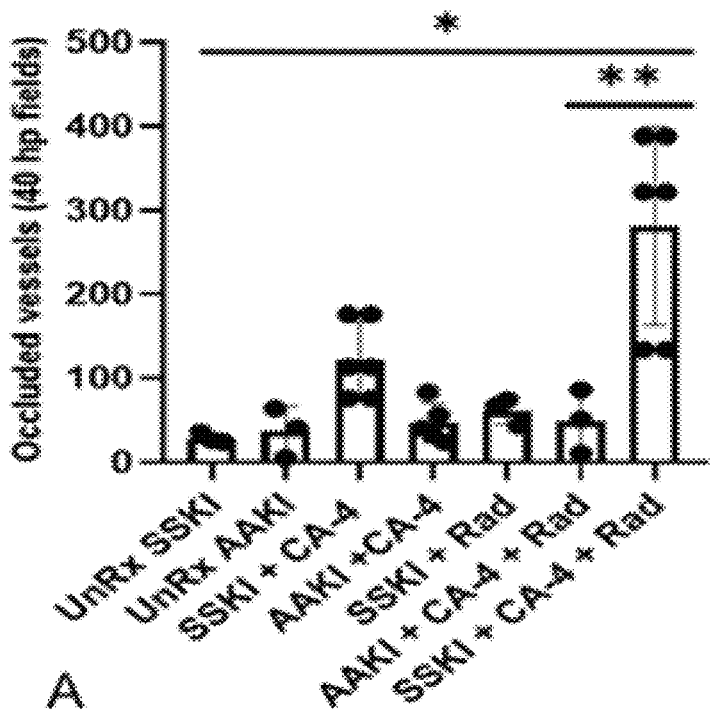
Figure 8:
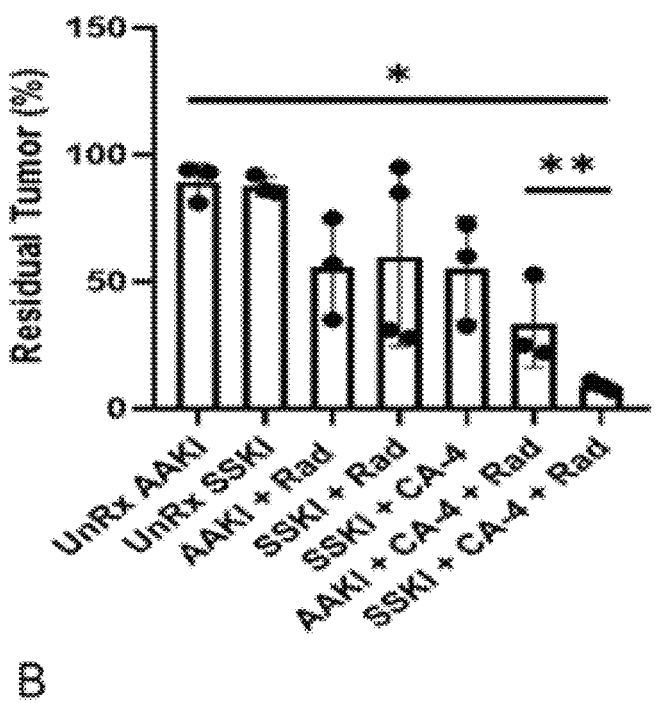

FIG. 8. Quantitation of vaso-occlusion and residual viable tumor in sections of established LLC obtained on day 20 from in SSKI and AAKI mice after treatment with tumor SR (10 Gy) on day 12 followed by CA-4 on days 13, 15 and 18 as described in Methods. (A) vessel closure in SSKI mice treated with radiation and CA-4 exceeded that of similarly treated AAKI mice (**p=0.003) and all other controls (*p≤0.003, n=4-6). (B) Residual viable LLC in sections obtained on day 20 from SSKI mice treated with sublethal radiation (10 Gy) on day 12 followed by CA-4 on days 12, 15 and 18 was significantly diminished relative to similarly treated AAKI mice (**p=0.005) and all other controls (*p<0.01, Student's t-test two-tailed). n=3.

Figure 9:
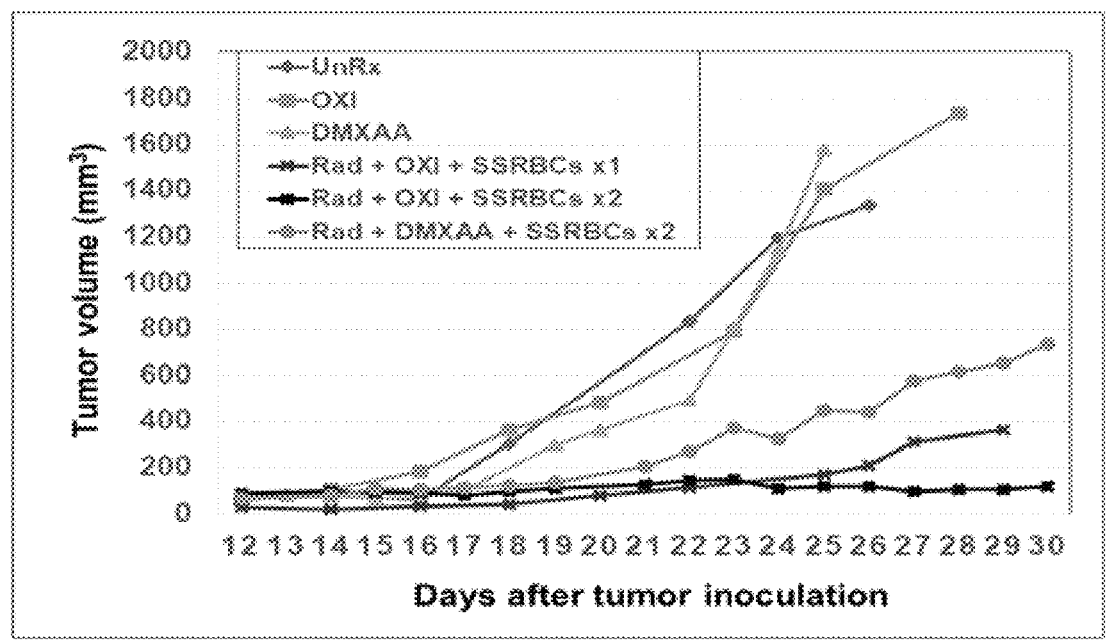
Figure 9:
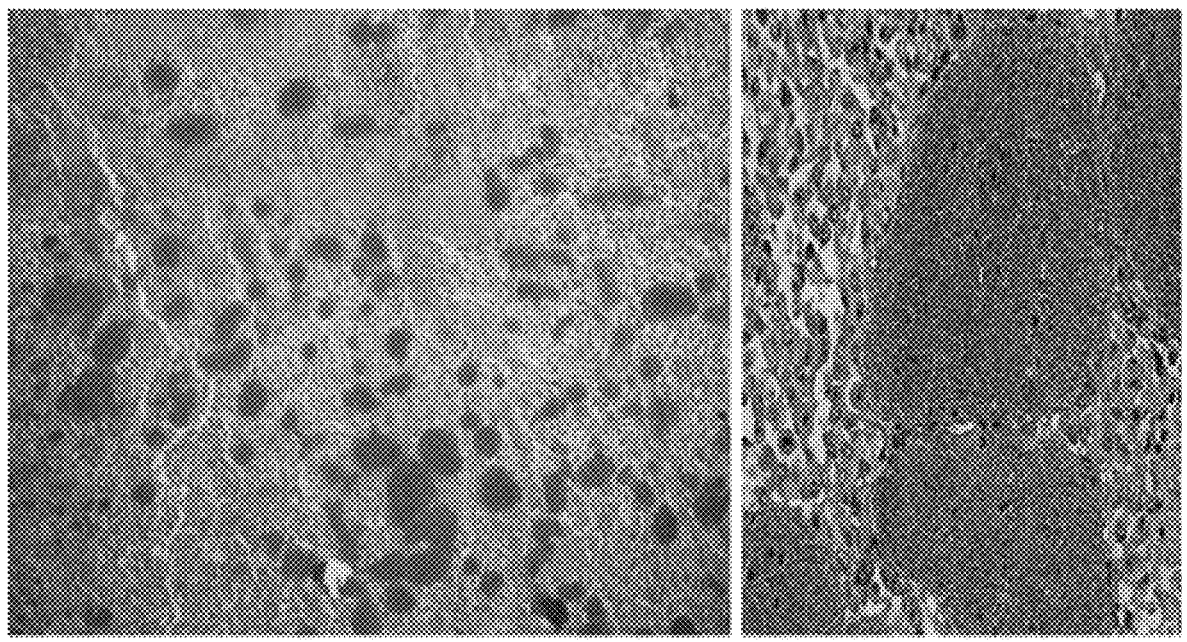

FIG. 9. (A) Complete growth delay of established LLC in C57BL/6 mice on day 30 after treatment with tumor SR (10 Gy) on day 12 followed by Oxi4503 or DMXAA plus passive infusion of human or mouse SSRBCs (triple therapy) on day 13 is shown. This cycle was repeated on days 21 and 21. Two cycles of treatment with the Oxi4503 regimen induced complete tumor growth delay and was superior to a single cycle (p=0.001). In addition, two cycles of the Oxi4503 regimen was superior to the DMXAA regimen in inducing tumor regression (P<0.001). (B) Section from mouse bearing established LLC on day 14 after treatment with radiation 10 Gy on day 12 followed by infusion of SSRBCs and Oxi4503 on day 13 shows disseminated tumor vaso-occlusion with erythrocytes displaying the sickle cell morphology trapped in occluded vessels. This associated with broadly propagated tumor infarction and tumor cell necrosis (H&E ×10 and ×25 magnification).

Figure 10:
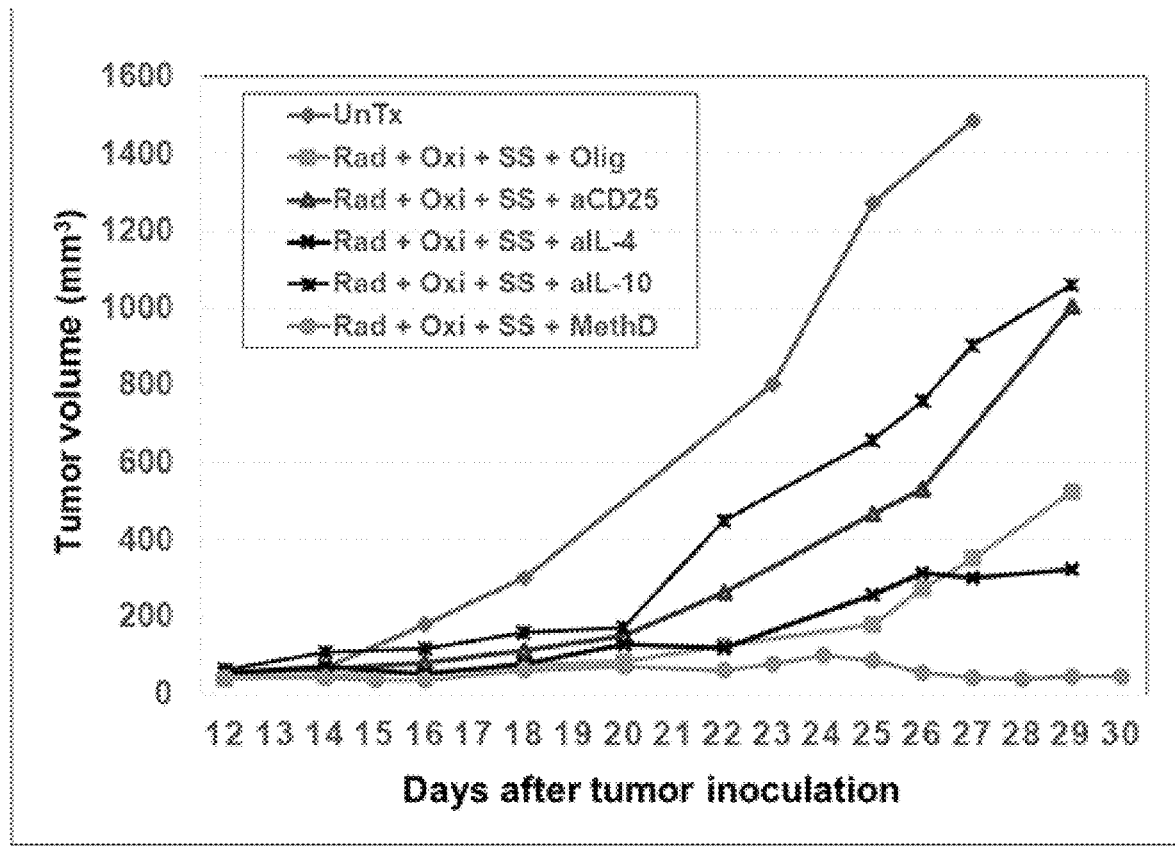

FIG. 10. Complete growth delay established LLC in C57BL/6 mice by addition of methionine depletion to the SSRBCs/Oxi4503/radiation regimen. Mice were treated with tumor SR (10 Gy) on day 12 followed by Oxi4503 plus passive infusion of human or mouse SSRBCs on day 13. Beginning on day 12 Methionine depletion was induced by a methionine deficient diet plus daily injections of FIDAS-5. The regimen induced complete tumor growth retardation on day 30 compared to the SSRBCs/Oxi4503/radiation program combined with individual immunotherapeutic agents anti-CD25, anti-IL4, anti-IL10 and Toll 9 oligonucleotide inhibitor (p<0.001).

Figure 11:
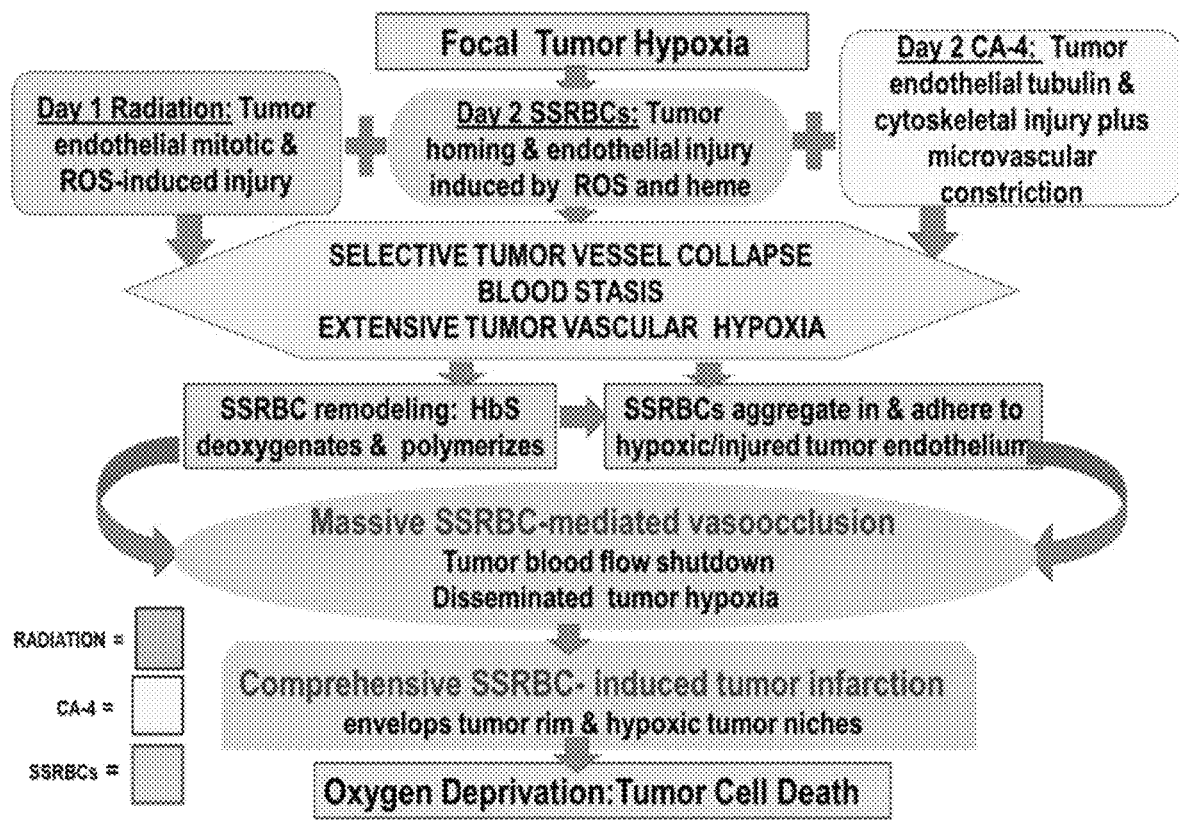

FIG. 11. Chain of events leading to massive SSRBCs-mediated tumor vaso-occlusion and infarction in tumor microvessels conditioned for tumor vascular injury by CA-4 and tumor SR is shown. Untreated LLC shows a modest degree of focal tumor hypoxia. Introduction of sublethal radiation initiates tumor endothelial mitotic-based and oxidant-mediated injury followed within 24 hours by CA-4 which induces endothelial tubulin depolymerization and cytoskeletal injury. Subsequent addition of SSRBCs and their contact with the tumor endothelium induces further oxidant-mediated damage. The combined effect results in severe tumor hypoxia and vascular injury resulting in blood flow stagnation. Under these conditions, HbS deoxygenates and polymerizes and the SSRBCs assume the sickle morphology forming aggregates that adhere to the tumor vessel wall. A surge of SSRBC-mediated tumor vaso-occlusion ensues with disseminated mononuclear cell infiltration and infarction. The scale of the tumor infarction engulfs the entire tumor including treatment-resistant hypoxic niches and the tumor rim. The comprehensive tumor eradication leads to tumor regression and a major histopathologic treatment effect.

DETAILED DESCRIPTION OF PREFERRED EMBODIMENTS

The invention is based, on the surprising and unexpected discovery that sickle cell infusions can prevent the regrowth or relapse of tumor growth that may occur following treatment of a solid tumor with a vascular disrupting agents (VDA). In particular, the inventors have discovered that SSRBC-induced tumor vaso-occlusion in solid tumors is dramatically increased when combined with a VDA and sublethal radiation (SR). For example, SSRBCs cause a rapid and pronounced increase in the number occluded tumor blood vessels after VDA treatment leading to tumor infarction. The resulting tumor necrosis engulfs treatment resistant hypoxic tumor niches and the tumor rim. Indeed, the inventor has made the surprising discovery that the addition of SSRBCs to VDA and SR therapy leads to complete tumor regressions and histologic obliteration of up to 95% of the tumor parenchyma. This result was highly unexpected since both SSRBCs, VDAs and SR individually induce only a modest degree of tumor vaso-occlusion and tumor progression. Indeed, the comprehensive scale of the tumoricidal response and complete tumor regressions could not have been predicted from the prior studies.

Sickle Cells Sickle cell anemia is a monogenic hemoglobinopathy wherein glutamic acid, the sixth amino acid in the β-globin chain, is displaced by valine (Rees D C, Lancet (2010) 376:2018-31 Kaul D K Microcirculation (2009) 16:97-111). This results in hemoglobin polymerization and sickling morphology during hemoglobin desaturation. Clinically, the disease is characterized by chronic hemolysis, intermittent vaso-occlusive events, and organ injury (Belcher Am J Physiol Heart Circ Physiol (2005) 288: H2715-25. Belcher J D, Blood (2014) 123:377-90). Endothelial cells are chronically activated and injured after contact with sickle cells, sickle cell-derived heme, and inflammatory mediators. Contributing to the microvascular injury and dysfunction are abundant reactive oxygen species (ROS) generated in the course of relentless ischemia-reperfusion, chronic hemolysis, and vascular inflammation (Hebbel R P. Hematol Oncol Clin N Am (2014) 28:181-98).

Sickle red blood cells (SSRBCs) as used in the subject compositions and methods may include their nucleated precursors and sickle hemoglobin variants. Sickle cells have shown an ability to home to tumor vasculature. This tumor localization is largely enabled by a disordered vasculature and severe hypoxia with $pO_2$ levels ranging from 1-10%. Pockets of these hypoxic tumor cells termed "hypoxic niches" are present in nearly all solid tumors and constitute a major cause of treatment resistance and tumor recurrence. Intravital microscopy observations show that infused SSRBCs home to established tumor, form aggregates in tumor vessels and induce focal vessel closure. Together with pro-oxidants or oncogenic virus, SSRBCs also produce a therapeutic tumor growth delay but fail to produce complete tumor regressions. The present invention shows that SSRBC-induced tumor vaso-occlusion is markedly enhanced when combined with a VDA and radiation resulting in complete tumor regressions From a physiologic standpoint, the hypoxic tumor microenvironment is a favorable site for SSRBC-induced vaso-occlusion. Under these hypoxic conditions SS hemoglobin polymerizes resulting in formation of membrane spicules and upregulation of a panoply or adhesion molecules. These molecules include BCAM/Lu, ICAM-4 and $\alpha_4\beta_1$ that adhere abnormally to cognate ligands laminin-a5, $\alpha_v\beta_3$, and VCAM-1 overexpressed on tumor endothelium. Such adhesion is amplified over time resulting in the formation of SSRBC microaggregates that obstruct/occlude tumor vessels. SSRBCs trapped on the tumor endothelium produce superoxide/peroxide-driven hydroxyl radicals leading to membrane peroxidation and hemolysis. Hemoglobin released from hemolyzed SS cells is rapidly oxidized from ferro- to ferri-hemoglobin (methemoglobin) generating highly lipophilic heme-nitrosyl complexes that readily intercalate into cell membranes. Such intracellular heme and its oxidative product free iron are highly toxic to cells catalyzing the oxidation of membrane lipids and DNA and activating caspases and cathepsins leading to perturbations of cytoskeleton and apoptosis. In this fashion, the SSRBCs by themselves are able to potentiate the tumoricidal effect of exogenously administered prooxidants (Terman D S et al. PLoS ONE 8(1): e52543. doi:10.1371 (2013)).

SSRBCs as used in the subject compositions and methods may obtained by methods known generally to persons of ordinary skill in the art such as manuel phelbotomy or leukopheresis or erythrocytapheresis with isolation of the SSRBCs from subjects with sickle cell anemia or sickle cell variants (Ullrich H et al. Transfusion Medicine and Hemotherapy. Vol. 35, 2007. pp. 25-30).

Manuel phlebotomy is the preferred methods of isolation of SSRBCs. One to two units of blood are obtained from subject with sickle cell anemia or sickle cell variant as with a conventional normal blood donor. The blood is collected in hepatized blood packs used routinely in blood banks.
1) Centrifuge whole blood at 500×g for 10 min at 4 degrees C.
2) Aspirate supernatant (plasma) and add cell wash buffer to erythrocyte pellet. Note: Ensure volume of cell wash buffers double the volume of erythrocyte pellet alone.
3) Centrifuge erythrocytes at 500×g for 10 min at 4° C.
4) Aspirate supernatant and add cell wash buffer to erythrocyte pellet. Note: Ensure volume of cell wash buffers double the volume of erythrocyte pellet alone.
5) Repeat steps 3 and 4 two more times for a total of 3 washes of the erythrocytes.

This wash procedure is adequate in acquiring a 70-80% hematocrit of human SSRBCs. If erythrocytes appear to be resuspending, increase the deceleration time of the centrifuge. The purity of erythrocyte preparations by this method has been confirmed by Wright staining and flow cytometry. The following references contain the general procedure and the cell wash buffers (Swerdlow P S Hematology 2006: 48-53 2006; Davis B A British Journal of Haematology, 2017, 176, 179-19; Hanson M S et al. Am. J. Physiol Heart Circ. Physiol 2008; 295:H786-H793)

Erythrocytapheresis is an additional mode of removing SSRBCs from patients with sickle cell anemia for use in the instant invention. This automated procedure entails the removal of the patient's red blood cells containing the abnormal sickle hemoglobin and replacing them with normal red blood cells carrying normal hemoglobin. In these procedures, the patient's plasma is not exchanged but is returned to the patient. The advantages of automated exchange transfusion have been recognised in a recent medical technology guidance published by the National Institute for Health and Care Excellence (NICE, 2016). NICE has recommended the use of the Spectra Optia Apheresis System (Terumo BCT, Lakewood, Colo., USA) for automated red cell exchange to remove sickle cells from patients with patients with sickle cell anemia. Quantities of SSRBCs suitable for use in the instant invention are obtained using this method. The technique is described in detail by Davis B A et al., British Journal of Haematology, 2017, 176, 179-19; Janes S L et al., British Journal of Haematology 1997, 97, 256-258; Lawson S E et al. Clinical and Laboratory Haematology 1999, 21, 99-102.
Kim H C et al. Blood, 1994, 83, 1136-1142)
Therapeutically Useful Sickle Erythrocytes are Obtained from Patients with Sickle Cell Anemia, Sickle Cell Trait and Sickle Cell Variants SSRBCs for use in the subject methods and compositions include erythrocytes containing at least one hemoglobin S allele are selected from a group consisting of erythrocytes containing SS hemoglobin, erythrocytes containing SA hemoglobin, erythrocytes containing SC hemoglobin, erythrocytes containing SD hemoglobin, erythrocytes containing SE hemoglobin, erythrocytes containing SAntilles hemoglobin and erythrocytes containing S beta plus thalassemia hemoglobin are useful in this invention.

For SS erythrocytes, sickling begins at $pO_2$ levels between 40-50 mmHg and is greatest when $pO_2<20$. This occurs in organs with sluggish circulation, high oxygen extraction, localized hypoxia and low pH such as the renal medulla and spleen and bone marrow. The likelihood of erythrocyte sickling by hemoglobin SS variants is related to amount of HgbS, e.g., Hgb S: 70-98%. Hgb SA: 10-40%, Hgb SC: 50-60%.

Sickle trait (SA hemoglobin) affects approximately 8% of the black population in the United States or approximately 2.7 million individuals. The incidence is higher in tropical Africa and approaches 40% in some regions. Patients with sickle trait are heterozygous for the sickle cell hemoglobin gene, and less than 50% of the hemoglobin in each cell is hemoglobin-S. Polymerization of deoxy-hemoglobin in erythrocytes from patients with SA hemoglobin can occur under certain conditions and transform silent sickle cell trait into a syndrome resembling sickle cell disease with vaso-occlusion. In particular, sustained exercise and high altitude conditions cause tissue hypoxia, acidosis, dehydration, hyperosmolality, hypothermia can cause splenic infarction, exertional heat illness (exertional rhabdomyolysis, heat stroke, or renal failure) or idiopathic sudden death. Because of their proclivity to sickle and aggregate in hypoxic tissues, erythrocytes with SA hemoglobin are useful in the present invention. Milosevic et al. *Gynecologic Oncology* 83, 428-431 (2001)) showed that erythrocytes from patients with sickle trait may sickle in the microvasculature of solid tumors and contribute to reduced blood flow and the development of hypoxia. Hypoxia is a strong independent prognostic factor in patients with cervix cancer. While this reference did not disclose the use of erythrocytes from patients with sickle cell trait for therapy of cancer, the skilled scientist would recognize that such cells can collect and aggregate under the hypoxic conditions within tumors in a fashion similar to homozygous SS sickle cell anemia. Similarly, under hypoxic conditions hemoglobins in erythrocytes from patients with other SS variants such hemoglobin SC, hemoglobin Antilles are known to polymerize leading to sickling and aggregation. Thus, this population of cells is also considered to be useful therapeutically and may be safe for transfusion since they do not sickle only under hypoxic conditions such as those encountered in tumors and not under normal physiologic conditions.

Erythrocytes with SC Hemoglobin

The coinheritance of HbS and HbSC results in a clinically significant sickling disorder similar to that of sickle cell disease (HbSS). HbSC disease is usually considered less severe than Hb SS disease however, some individuals manifest a condition equal in severity. HbSC disease exhibits combined symptomatology of both Hb S and Hb C diseases independently. Like SS disease, SC erythrocytes sickle under hypoxic conditions causing vaso-occlusion in ischemic tissues resulting in stroke, acute chest syndrome (chest pain, fever, dyspnea, and hypoxia), joint necrosis (especially head of femur and humerus), pain crises, acute and chronic organ dysfunction/failure, retinal hemorrhages, and increased risk of infection. Because SC erythrocytes sickle under ischemic conditions, they too are excellent candidates for use in the instant invention.

Erythrocytes with Hemoglobin S Antilles.

Hemoglobin S Antilles show two mutations in hemoglobin S gene. The expected mutation of glutamic acid to valine at position (3-6 similar to hemoglobin S is accompanied by a second substitution at position (3-23 of valine to isoleucine. Since the mutation at (3-23 produced no chance in the charge of the hemoglobin, it separated identically to hemoglobin S by standard techniques. Hemoglobin S Antilles is much less soluble than hemoglobin S. The consequence is that people heterozygous for hemoglobin A and hemoglobin S Antilles have symptoms and complications similar to those of patients with homozygous sickle cell disease. Because Hgb S Antilles erythrocytes sickle under hypoxic conditions, these cells are also excellent candidates for use in the present invention.

Nucleated erythroid precursors from patients with sickle cell anemia are the useful in the claimed subject matter. Because they possess nuclei, they are readily transduced with the therapeutic oncolytic viruses and nucleic acids encoding toxins, toxin-tumor specific antibodies, -diabodies, -nanobodies and other therapeutic molecules The hemoglobin of these cells polymerizes and they undergo characteristic morphological deformation in the form of fine, fragile, elongated spicules consisting of highly organized and tightly aligned hemoglobin fibers in the protruded regions. The nucleated erythroblasts have a larger volume than mature red cells and have more dilute hemoglobin which is confined mostly to the cytoplasm. Nevertheless, under partial or complete deoxygenation they behave much like mature SS red cells, i.e., they deposit and aggregate in the tumor microcirculation.

Therapeutically Useful Mature Sickle Cells, Nucleated Sickle Cell Precursors or Progenitors The present invention comprises the use of mature sickle erythrocytes or sickle cell variant disease as described herein as well as sickle cell erythroid precursor or progenitor cells. These cell are obtained from peripheral blood or bone marrow of subjects with sickle cell disease. They are also obtained from induced pluripotent stem cells (iPPSCs), pluripotent stem cells (PSCs), embryonic stem cells (ESCs), umbilical cord blood (UCB), hematopoietic stem/progenitor, erythroid precursor cells (HSPCs) derived from patients with sickle cell anemia or sickle cell variants as described in Table 1 below and in the following references (Seo Y et al. Stem Cells International Volume 2019, doi.org/10.1155/2019/9281329; Huang X et al. Molecular Therapy vol. 22 no. 2, 451-463 February 20141).

K et al. Cell, vol. 126, no. 4, pp. 663-676, 2006; Park I H, et al. Nature, vol. 451, no. 7175, pp. 141-146, 2008). As described above, iPSCs then undergo directed differentiation into the target lineage using specific growth factors and morphogens. "Direct conversion" in another option wherein several cell type-specific master TFs that initiate and/or govern the differentiation procedure are introduced to somatic cells. These cell undergo reprogramming to the intended lineage without going through a pluripotent state. Using this technique, several stem cell types have been successfully transdifferentiated from somatic cells (Han D W et al. Cell Stem Cell, vol. 10, no. 4, pp. 465-472, 2012; Song D Q et al. Cell Stem Cell, vol. 18, no. 6, pp. 797-808, 2016; Lalit P A et al. Cell Stem Cell, vol. 18, no. 3, pp. 354-367, 2016). To reprogram the fate of somatic cells into the hematopoietic lineage the most frequently used reprogramming factors are hematopoiesis-governing transcription factors Gata2, Lmo2, Tall, Scl, Fos, GfiB, and Erg which should be combined (Pereira C F et al Cell Stem Cell, vol. 13, no. 2, pp. 205-218, 2013; Batta K et al. Cell Reports, vol. 9, no. 5, pp. 1871-1884, 2014; Gomes A M et al., Cell Reports, vol. 25, no. 10, pp. 2821-2835.e7, 2018). The transcription factor-induced reprogramming strategy is also applicable to ESCs and iPSCs to enhance their conversion efficiency into HPSCs. The homeodomain TF HoxB4 and its related regulator Cdx4 are known to promote the hemogenic induction in PSCs both in vitro and in vivo. The differentiation potential of PSC-derived HSPCs can be directed by TFs. It is reported that the Gata2 and Tall-stimulated ESCs led to skewed differentiation towards the erythroid lineage (Bowles K M Stem Cells, vol. 24, no. 5, pp. 1359-1369, 2006; Wang Y, PNAS, vol. 102, no. 52, pp. 19081-19086, 2005; Shi X, Dev. Bio., vol. 389, no. 2, pp. 208-218, 2014).

Circulating HSPCs can generate SSRBCs. Circulating HSPCs can be directly obtained from the bone marrow or blood collection. Due to the invasiveness of the bone marrow-harvesting procedure, PB and UCB are regarded as the most common sources for CD34+ HSPCs and ex vivo-

TABLE 1

Current cell sources and strategies for ex vivo HBC generation.

| | Cell source | | | |
|---|---|---|---|---|
| PSCs | | Circulating cells | | Immortalized RBC |
| ESCs | iPSCs | UCB | PB | lines |
| | | Strategy | | |
| PSCs are differentiated into hematopoietic lineage to generate RBCs | | CD34+ HSPCs are isolated from the blood | | HSPCs or erythroid progenitors are immortalized |
| Pros (i) Superior expansion potential (ii) Established quality control criteria for GMP grade | (i) Superior expansion potential (ii) Suitable for donor-specific transfusion | (i) Dierect source for HSPCs (ii) Established quality control criteria for GMP grade (ii) Contains primitive HSPCs than PB | (i) Direct source for HSPCs (ii) RBCs from PB have more mature, adult-like phenotypes | (i) Theoretically unlimited expansion potential (ii) Applicable for further gene editing |

PSC: pluripotent stem cell; ESC: embryonic stem cell; iPSC: induced pluripotent stem cell; UCB: umbilical cord blood; PB: peripheral blood; HSPC: hematopoietic stem/progenitor cell.

iPSC generation involves the conversion of fully differentiated cells into ESC-like primitive pluripotent stem cells. With defined four transcription factors, Oct3/4, Sox2, Klf4, and c-Myc, it is possible to reverse the developmental process and reoriented somatic cell fate to iPSCs (Takahashi produced RBCs. In addition, mononuclear cells isolated from buffy coats of blood donations could be differentiated into RBCs (Douay L et al. Bulletin de l'Académie Nationale de Mëdecine, vol. 189, no. 5, pp. 903-913, 2005; Giarratana M C et al., Nature Biotechnology, vol. 23, no. 1, pp. 69-74, 2005; Timmins N E et al. Trends in Biotechnology, vol. 27, no. 7, pp. 415-422, 2009; Masiello F et al. Transfusion, vol. 54, no. 4, pp. 1059-1070, 2014).

Optimization of cells and growth factors promotes differentiation of PB-derived CD34+ cells to enucleated RBCs. The former cells can be cocultured with telomerase gene-transduced human stromal cells to expand the HSPC population. These cells can be differentiated into erythroblasts using a conventional liquid culture method then cocultured with macrophages from the third to the fourth phase for further expansion and maturation of SSRBCs. This method achieved an approximately $10^6$-fold expansion of the erythroblast from a single CD34+ cell. Moreover, the final phenotypical analysis on culture day 38 revealed that the coculture with a macrophage could increase the enucleated erythrocyte proportion in the total cells by 40-70% to over 99%. Thus, theoretically, about 3 transfusion SSRBC units ($6 \times 10^{12}$ RBCs) can be generated from only $5-6 \times 10^6$ of PB-isolated CD34+ cells (Fujimi A et al. International Journal of Hematology, vol. 87, no. 4, pp. 339-350, 2008).

Recently, a bioreactor system has been applied for the large-scale in vitro cell generation. Theoretically, over 500 transfusable SSRBC units can be generated from only five million CB-derived CD34+ cells using the bioreactor method (Y. Martin Y et al. Biomaterials, vol. 26, no. 35, pp. 7481-7503, 2005; Timmins N E et al. Tissue Engineering. Part C, Methods, vol. 17, no. 11, pp. 1131-1137, 2011).

Blood-derived erythroblasts genetically modified for immortalization of
is an additional technique for ex vivo generation of SSRBCs and SSRBC variants. HSPCs and committed erythropoietic progenitors isolated from UCB or PB gradually cease proliferating within 2-3 weeks of culture and start to differentiate
into mature RBCs. Thus, cell cycle regulators and pluripotency-inducing factors are common candidates for the genetic manipulation to maintain cell division as well as other immortalization strategies. Genetic engineering with reprogramming factors or hematopoietic regulators could convert primary erythroblasts into an immortalized cell line, which potentiates the feasibility of ex vivo production of SSRBCs in the clinical field (Huang H et al. Molecular Therapy, vol. 22, no. 2, pp. 451-463, 2014; Geiler C et al. International Journal of Stem Cells, vol. 9, no. 1, pp. 53-59, 2016; Trakarnsanga K et al., Nature Communications, vol. 8, no. 1, article 14750, 2017).

Recently, Hawksworth et al. have demonstrated a proof of concept to improve erythrocyte compatibility using a gene editing technique wherein the 5 major blood group antigens including KEL, RHAG, ACKR1, FUT1, and GYPB were ablated from the immortalized erythroid cell line BEL-A via combinational gene targeting with the CRISPR-Cas9 system to minimize safety issues related to incompatible transfusion. The authors successfully generated multiple knockout erythroid lines without any off-target mutations and confirmed the ablation of each antigen expression using an indirect antiglobulin assay. Importantly, no noticeable physiological change during the differentiation and maturation process was observed in knockout cells compared to normal RBCs. This suggests that SSRBCs devoid of blood group expression can be manufactured in a large scale from immortalized SSRBC and SSRBC variant lines (Hawksworth J et al. EMBO Molecular Medicine, vol. 10, no. 6, article e8454, 2018). In this context, similar gene editing technology can also be used to delete AA hemoglobin genes in iPPSCs and ESCs and replace them with SS hemoglobin.

Nucleated erythroid precursors from patients with sickle cell anemia can be readily obtained in abundance by culture of peripheral blood erythrocytes with erythropoietin (Fibach et al, Exp Hematology 26:319-319 (1998); Fibach et al. Blood 73: 100-103 (1989)). Peripheral blood (10-20 ml) is drawn from patients with sickle cell anemia and mononuclear cells isolated by centrifugation on a gradient of Ficoll-Hypaque are cultured according to a two phase liquid culture procedure. In phase 1, the cells are cultured for 7 days in a-minimal essential medium supplemented with 10% fetal calf serum (both from Gifco, Grand Island N.Y.), cyclosporine A (1 pg/ml) (Sandoz, Basel, Switzerland) and 10% conditioned medium collected from bladder carcinoma cultures. In phase 2, the nonadherent cells are recultured in a medium supplemented with 30% fetal calf serum, 1% deionized bovine serum albumin, 2-mercaptoethanol, glutamine, dexamethasone, and human recombinant erythropoietin (Ortho Pharmaceutical Co., Raritan N.J.). Cultures are incubated at 37° C. in an atmosphere of 5% CO to air with extra humidity. Cell morphology is assessed microscopically on cytocentrifuge-prepared slides (Shandon, Cheshire, U K) stained with alkaline benzidine and Giemsa.

The therapeutically effect dose of sickle cells varies from 50 to 500 ml and is administered parenterally preferably intravenously over a period of 10 minutes to 3 hours. The sickle cells are used as part of combinatorial treatment with a vascular disrupting agent (VDA) and radiation as described below. The preferred treatment is to deliver radiation to the tumor followed within 4-48 hours by the injection of a VDA and sickle cell infusions. The latter two modalities are given at about the same time or the sickle cells are adminstered 30 minutes to four hours after VDA treatment. In another embodiment, the sickle cells may be administered intravenously simultaneously with VDA. The sickle cells are administered intravenously or intraarterially in a volume of 5-500 ml over 30 minutes to 3 hours in fashion identical to a typical blood transfusion as described under Pharmaceutical Preparations.

Vascular Disrupting Agents (VDAs): Combretastatins and Combretastatin Prodrugs

The instant invention contemplates the use of a vascular disrupting agent that falls within the structural and functional scope of the combretastatins or combretastatin prodrugs. These agents are used together with sickle cells or its variants and radiation therapy to produce a potent tumoricidal response and tumor regression. They are also useful when methionine depletion therapy is added to this regimen. Vascular Disrupting Agents ("VDAs), also known as vascular damaging agents or vascular targeting agents, are a separate class of ant vascular chemotherapeutics. The vascular mediated cytotoxic mechanism of VDA action differs from that of anti-angiogenic agents, which inhibit the formation of new tumor vascularization rather than interfering with the existing tumor vasculature. Other agents have been known to disrupt tumor vasculature but differ in that they also manifest substantial normal tissue toxicity at their maximum tolerated dose. In contrast to anti-angiogenic drugs, VDAs attack solid tumors by selectively targeting the established tumor vasculature and causing extensive shutdown of tumor blood flow. A single dose of a VDA can cause a rapid and selective induction of hypoxia and nutrient depletion. Genuine VDAs retain their vascular shutdown activity at a fraction of their maximum tolerated dose. CA-4, and other combretastatins (e.g. combretastatin A-1 (CA-1)) have been shown to bind a site at or near the colchicine binding site on tubulin with high affinity. Tubulin-binding VDAs selectively destabilize the microtubule cytoskeleton of tumor endothelial cells, causing a profound alteration in the shape of the cell which ultimately leads to occlusion of the tumor blood vessel and shutdown of blood flow to the tumor (Kanthou et al., Blood, 2002; Cooney et al., Curr Oncol Rep. 2005 7(2): 90-5; Chaplin et al., Curr Opin Investig Drugs, (2006), 7(6):522-8).

A particularly promising subclass of VDAs are the combretastatins. Derived from the South African tree *Combretum caffrum*, combretastatins such as combretastatinA-4 (CA-4) were initially identified in the 1980's. This family of natural products includes several synthetic derivatives and analogues. In vitro studies clearly demonstrated that combretastatins are potent cytotoxic agents against a diverse spectrum of tumor cell types in culture. However, CA-4 does not display the expected activity in vivo due to its poor bioavailability caused by its low solubility and the instability of its cis conformation, which easily changes to form the trans-isomer. Phosphates as prodrugs of combretastatins show better aqueous solubility and importantly, they are metabolized to their active forms by phosphatase, which exerts high activity in the tumor environment. CA4P and CAP, respective phosphate prodrugs of CA-4 and CA-1, were subsequently developed to combat problems with aqueous insolubility (see U.S. Pat. Nos. 4,996,237; 5,409,953; and 5,569,786, each of which is incorporated herein by reference).

The primary mechanism of action of VDAs is "vascular targeting". The inhibition of microtubule assembly in endothelial cells lining tumor-feeding vasculature, leads to a series of cell signaling events that ultimately result in disrupted endothelial cell morphology and blood flow reduction. The inhibition of tubulin polymerization results in activation of RhoA, an intracellular coordinator of the cytoskeletal rearrangement of microtubules and actin, and leads to transient decrease or complete shutdown of tumor blood flow that results in secondary tumor cell death due to hypoxia, acidosis, and/or nutrient deprivation (Dark et al., Cancer Res., 57: 1829-34, (1997); Chaplin et al., Anticancer Res., 19:189-96, (1999); Hill et al., Anticancer Res., 22(3): 1453-8 (2002); Holwell et al., Anticancer Res., 22(2A):707-11, (2002).; Holwell et al., Anticancer Res., 22(2A):707-11, (2002). CAP and CA4P cause a rapid and acute shutdown of the blood flow to tumor tissue that is separate and distinct from the anti-proliferative effects of the agents on tumor cells themselves. Blood flow to normal tissues is generally far less affected by CA4P and CA1P than blood flow to tumors. While effective in killing the vast majority of the tumor mass, some tumors are nonetheless resistant to treatment with VDAs, such as combretastatin A-4 phosphate (CA4P), due to a rim of viable tumor tissue, which can serve to repopulate the tumor, eventually leading to progression of tumor cell growth (Dark et al., Cancer Res., 57: 1829-34, (1997); Chaplin et al., Anticancer Res., 19:189-96, (1999)). This rim of surviving cells is most likely a consequence of the shared normal vessel circulation between the perimeter of tumors and neighboring normal tissue. Rapid tumor regrowth from the treatment resistant tumor rim generally precludes tumor regression. There is thus an urgent need in the art to provide methods to improve VDA therapy by preventing tumor regrowth. The instant invention provides a cure for this problem. The addition of sickle cells or its variants plus radiation CA4P or CA1P inhibits tumor regrowth from this rim of viable cells and produces complete tumor regressions.

As used herein, the term "combretastatin agent" or "combretastatin' denotes at least one member of the combretastatin family of compounds, derivatives or analogs thereof, their prodrugs (preferably phosphate prodrugs) and derivatives thereof, and salts of these compounds. Combretastatins include those anti-cancer compounds isolated from the South African tree *Combretum caffrum*, including without limitation, Combretastatins A-1, A-2, A-3, A-4, B-1, B-2, B-3, B-4, D-1, and D-2, and various prodrugs thereof, exemplified by CombretastatinA-4 phosphate (CA4P) compounds, Combretastatin A-1 diphosphate (CA1P) compounds and salts thereof (see for example Pettit et al., Can. J. Chem. (1982); Pettit et al., J. Org. Chem., 1985; Pettit et al., J. Nat. Prod, 1987; Lin et al., Biochemistry, (1989); Pettit et al., J. Med. Chem., 1995; Pettit et al., Anticancer Drug Design, (2000); Pettit et al., Anticancer Drug Design, 16(4-5): 185-93

Combretastatin A-4

Methods and compositions of the subject invention can employ one more more different species of combretastatin molecules. It will be understood by persons skilled in the art that the use combrestatins includes the use of the prodrug form of the combretastatins. Molecules that fall into the combretastatin family generally share 3 common structural features: a trimethoxy "A"-ring, a "B"-ring containing substituents often at C3' and C4, and [often] an ethene bridge between the two rings which provides necessary structural rigidity as shown below. Molecules with such an ethene bridge are also stilbenoids, molecules with a non-ethene bridge are dihydrostilbenoids as shown below.

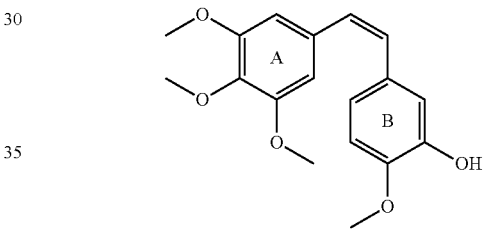

Molecules with C3' amino and hydroxyl substituents are very active, and molecules with C4' hydroxyl or methoxy substituents are also cytotoxic. Of the natural products presently known combretastatin A-4 is the most potent in regard to both tubulin binding ability and cytotoxicity. Combretastatin A-1 is also a potent cytotoxic agent. Another molecule is combretastatin B-1.

As used herein, the term combretastatin A-4 phosphate (CA4P) denotes as least one of combretastatin A-4 phosphate prodrugs, derivatives thereof, and salts of these compounds. As used herein, the term combretastatin A-1 diphosphate (CA1P) compound denotes as least one of combretastatin A-1 diphosphate prodrugs (e.g., OXi4503), derivatives thereof, and salts of these compounds.

As used herein, the term "prodrug" refers to a precursor form of the drug which is metabolically converted in vivo to produce the active drug. Thus, for example, combretastatin phosphate prodrug salts administered to an animal in accordance with the present invention undergo metabolic activation and regenerate combretastatin A-4 or combretastatin A-1 in vivo, e.g., following dissociation and exposure to endogenous non-specific phosphatases in the body. Preferred prodrugs of the present invention include the phosphate, phosphate ester, phosphoramidate, phosphoramidate ester, or amino acid acyl groups as defined herein. Exemplary phosphate esters include —OP(O)(O-alkyl) or salts of the phosphate group, for example —OP(O)(ONH). In preferred embodiments, a prodrug of the invention comprises a substitution of a phenolic moiety or amine moiety of the active drug with a phosphate, phosphoramidate, or amino acid acyl group. A wide variety of methods for the preparation of prodrugs are known to those skilled in the art (see, for example, Pettit and Lippert, Anti-Cancer Drug Design, (2000), 15, 203-216).

Other exemplary prodrugs of combretastatin agents include the cyclic phosph(oramid)ate prodrugs described in U.S. Pat. Nos. 7,205,404 and 7,303,739, which are incorporated by reference herein. Exemplary combretastatin derivatives retain cis-stilbene as a fundamental skeleton and exhibit tubulin polymerization inhibiting activity of 10 micromolar or less (e.g., 1 micromolar, 0.1 micromolar, 10 nanomolar, 1 nanomolar or less).

The structures of the parent combretastatin, its derivatives and prodrugs are shown below.

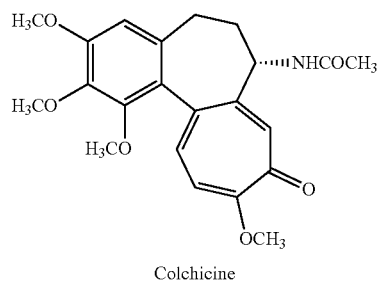

Colchicine

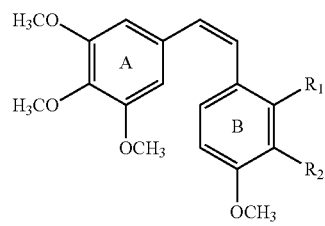

Combretastatin Natural Products and Analogues
Combretastatin A-4 (CA4): $R_1 = H$; $R_2 = OH$
Combretastatin A-4P (CA4P): $R_1 = H$; $R_2 = OPO_3Na_2$
Combretastatin A-1 (CA1): $R_1 = R_2 = OH$
Combretastatin A-1P (OX34503): $R_1 = R_2 = OPO_3Na_2$
2' CA4-amine: $R_1 = NH_2$; $R_2 = H$
CA1-diamine: $R_1 = R_2 = NH_2$
3' CA4-amine: $R_1 = H$; $R_2 = NH_2$

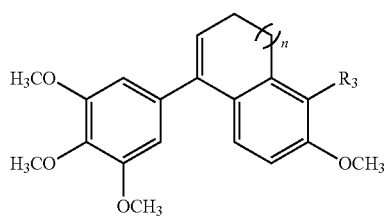

Fused-Ring Analogues
Dihydronaphthalene phenol (OXi6196): $n = 1$; $R_3 = OH$
Dihydronaphthalene amine (KGP05): $n = 1$; $R_3 = NH_2$
Benzosuberene phenol (KGP18): $n = 2$; $R_3 = OH$
Benzosuberene amine (KGP156): $n = 2$; $R_3 = NH_2$

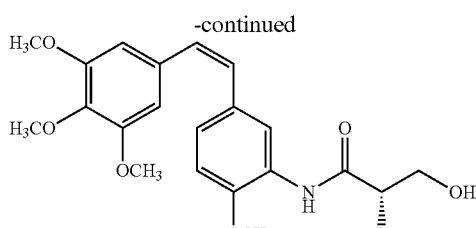

3' CA4-$L$-serinamide: $R_4 = NH_2$
AVE8062: $R_4 = NH_2 \cdot HCl$

Exemplary combretastatin salts contemplated for use in the methods of the invention are described in WO99/35150; WO 01/81355; U.S. Pat. Nos. 6,670,344; 6,538,038: 5,569,786; 5,561,122; 5,409,953: 4,996,237 which are incorporated herein by reference in their entirety. Exemplary combretastatin derivatives or analogs of combretastatins are described in Singh et al., J. Org. Chem., 1989; Cushman et al., J. Med Chem., 1991: Getahun et al., J. Med. Chem., 1992; Andres et al. Bioorg. Med. Chem. Lett., 1993; Mannila, et al., Liebigs. Ann. Chem., 1993; Shirai et al., Bioorg. Med. Chem. Lett., 1994; Medarde et al., Bioorg. Med. Chem. Lett., 1995; Wood et al, Br. J. Cancer, 1995; Bedford et US 2008/0214509 A1; Dorr et al., Invest. New Drugs, 1996; Jonnalagadda et al., Bioorg. Med. Chem. Lett., 1996; Shirai et al., Heterocycles, 1997: Aleksandrzak, et al., Anti-cancer Drugs, 1998; Chen et al., Biochem. Pharmacol., 1998; Ducki et al., Bioorg. Med. Chem. Lett., 1998: Hatanaka et al., Bioorg Med. Chem. Lett., 1998; Medarde et al., Eur: J. Med. Chem., 1998; Medina et al., Bioorg. Med. Chem. Lett., 1998; Ohsumi et al., Bioorg. Med. Chem. Lett., 1998; Ohsumi et al., J. Med. Chem., 1998: Pettit, et al., J. Med. Chem., 1998: Shirai et al., Bioorg Med. Chem. Lett., 1998: Banwell et al., Aust. J. Chem., 1999; Medarde et al., Bioorg. Med. Chem. Lett., 1999: Shan et al., PNAS, 1999; Combeau et al., Mol. Pharmacol., 2000; Pettit et al., J. Med Chem., 2000; Pinney et al., Bioorg. Med. Chem. Lett., 2000; Flynn et al., Bioorg. Med. Chem. Lett., 2001; Gwaltney et al., Bioorg Med. Chem. Lett., 2001; Lawrence et al., 2001; Nguyen-Hai et al., Bioorg. Med. Chem. Lett., 2001; Xia et al., J. Med. Chem., 2001; Tahir et al., Cancer Res., 2001; Wu-Wong et al., Cancer Res., 2001; Janiketal, Bioorg. Med. Chem. Lett., 2002; Kim et al., Bioorg Med Chem. Lett., 2002: Li et al., Bioorg. Med. Chem. Lett., 2002: Nam et al., Bioorg Med. Chem. Lett., 2002; Wang et al., J. Med. Chem. 2002; Hsieh et al., Bioorg. Med. Chem. Lett., 2003; Hadimani et al., Bioorg. Med. Chem. Lett., 2003; Mu et al., J. Med. Chem, 2003; Nam et al., Curr. Med. Chem., 2003: Pettit et al, J. Med. Chem., 2003; Gaukroger et al., Org Biomol Chem. 2003: Bailly et al., J Med Chem. 2003: Sun et al., Anticancer Res. 2004; Sun et al., Bioorg Med Chem Lett. 2004; Liou et al., J Med Chem. 2004; Perez-Melero et al., Bioorg Med Chem Lett. 2004; Liou et al., J Med Chem. 2004: Mamane et al., Chemistry. 2004; De Martini et al., J Med Chem. 2004: Ducki et al, J Med Chem. 2005; Maya et al., J Med Chem. 2005; Medarde et al., J Enzyme Inhib Med Chem. 2004; Simoni et al, J Med Chem. 2005; Sanchez et al., Bioorg Med Chem. 2005; Vongvanich et al., Planta Med. 2005: Tron
et al., J Med Chem. 2005; Borrel et al., Bioorg Med Chem. 2005; Hsieh et al., Curr Pharm Des. 2005; Lawrence et al, Curr Pharm Des. 2005; Hadfield et al., Eur J Med Chem. 2005; Pettit et al J Med Chem. 2005; Coggioloa et al., Bioorg Med Chem Lett. 2005; Kaffy et al., Org Biomol Chem. 2005; Mateo et al., J Org Chem. 2005; LeBlanc et al., Bioorg Med Chem. 2005; Srivistava et al., Bioorg Med Chem. 2005; Nguyen et al., J Med Chem. 2005; Kong et al., Chem Biol. 2005; Li et al, Bioorg Med Chem Lett. 2005; Pettit et al, J Nat Prod. 2005; Nicholson et al. Anticancer Drugs. 2006; Monk et al., Bioorg Med Chem. 2006; De Martino et al., J Med Chem. 2006: Peifer et al., J Med Chem. 2006; Kaffy et al., Bioorg Med Chem. 2006: Banwell et al., Bioorg Med Chem. 2006; Dupeyre et al., Bioorg Med Chem. 2006 Simoni et al, J Med Chem. 2006; Tron et al., J Med Chem. 2006; Romagnoli et al., J Med Chem. 2006: Pandit et al., Bioorg Med Chem. 2006; Nakamura et al., Chem Med Chem. 2006: Pirali et al., J
MedChem. 2006: Bellina et al., Bioorg Med Chem Lett. 2006; Hu et al, J Med Chem. 2006; Chang et al., J Med Chem. 2006; Thomson et al., Mol Cancer Ther: 2006; Fortin et al., Bioorg Med Chem Lett., 2007: Duan et al., J Med Chem., 2007: Zhang et al., J Med Chem. 2007; Wu et al., Bioorg Med Chem Lett. 2007: Sun et al., Bioorg Med Chem Lett. 2007, WO07/140,662; WO 07/059,118; WO 06/138427; WO06/036743: WO 05/007635, WO 03/040077, WO 03/035008, WO 02/50007, WO 02/14329; WO 01/12579, WO 01/09103, WO 1/81288, WO 01/84929, WO 00/48590, WO 00/73264, WO 00/06556, WO 00/35865, WO 99/34788, WO 99/48495, WO 92/16486, U.S. Pat. Nos. 7,312,241; 7,223,747; 7,220,784; 7,135,502; 7,125,906; 7,105,695; 7,105,501; 7,087,627;

Combretastatins

General Synthesis Procedure

A variety of possible routes to the combretastatin skeleton are possible. One reasonably easy synthesis is as follows:
- 1-Bromomethyl-3,4,5-trimethoxybenzene undergoes an $S_N2$ reaction with triphenylphosphine, which yields a phosphonium salt.
- This compound, through an ylide intermediate, is coupled to a benzaldehyde-derived B-ring possessing the desired substituents using a Wittig olefination.
- The Wittig reaction produces varying amounts of E and Z isomers depending mainly on solvent polarity, temperature, metal cation coordination effects, and the electronic effect of substituents on either the triphenylphosphine salt or the benzaldehyde. Generally cis-combretastatin possesses significantly improved ability to inhibit tubulin polymerization as well as cytotoxicity.
- To directly generate the cis forms a Perkin condensation reaction can be used.

Preferred Combretastatin Prodrugs in the Instant Invention

AVE8062 (CA-4, Ombrabulin, AC7700H)

General

AVE8062 is the serine prodrug of the tubulin binding agent CA4. The parent compound is released upon exposure to amino peptidase. AVE8062 was found to have more powerful tumor blood flow (TBF) stasis effects and antitumor effects compared with CA4P. AVE8062 causes shape changes in proliferating endothelial cells, rapid shutdown of tumor blood flow, and extensive
necrosis in experimental tumor models. However, despite the strong tumor-suppressing qualities of AVE8062, it does not produce an immediate reduction in tumor size upon administration.

In one exemplary embodiment, a combretastatin derivate is the amine or serinamide derivative of CA4, e.g. AVE8032. Preclinical studies
have proved the high anti-mitotic and vascular disrupting potency of this
compound. AVE8062 is an amino acid prodrug. It is the serinamide of (Z)-2-methoxy-5-[2-(3,4,5-trimethoxyphenyl) vinyl]phenylamine (CS-39), a synthetic amino-combretastatin with the 3-hydroxy group in CA4 replaced by a 3-amino group. From a series of synthetic analogs designed to improve the solubility profile of CA4, the amino-combretastatin CS-39 was identified to have potent antitubulin activity and cytotoxicity. Wittig reaction of 3,4,5-trimethoxybenzyl phosphonium bromide with 4-methoxy-3-nitrobenzaldehyde produced a 1:1 mixture of (E)- and (Z)-isomers. The (Z)-isomer was obtained by crystallization, followed by reduction using Zn to produce the amine CS-39. CS-39 was found to have significant antitumor activity in the Colon 26, Colon 38 and 3LL tumor models, as well as in human xenograft HCT-15 model. To further improve the water solubility of CS-39, a group of amino acid prodrugs were prepared, via reaction of the amine with a protected amino acid, followed by removal of the protecting group(s). AVE8062 (CS-39-L-Ser HCI, AC7700) was found to have improved solubility and could be easily formulated for in vivo studies. The amide prodrug was cleaved to generate the parent compound CS-39 in the whole blood of mice and human, probably by the action of amino peptidases. AVE8062 was found to have enhanced antitumor activity and decreased toxicity in a Colon 26 murine adenocarcinoma model. The synthetic scheme for CD39 and AVE8062 is shown below.

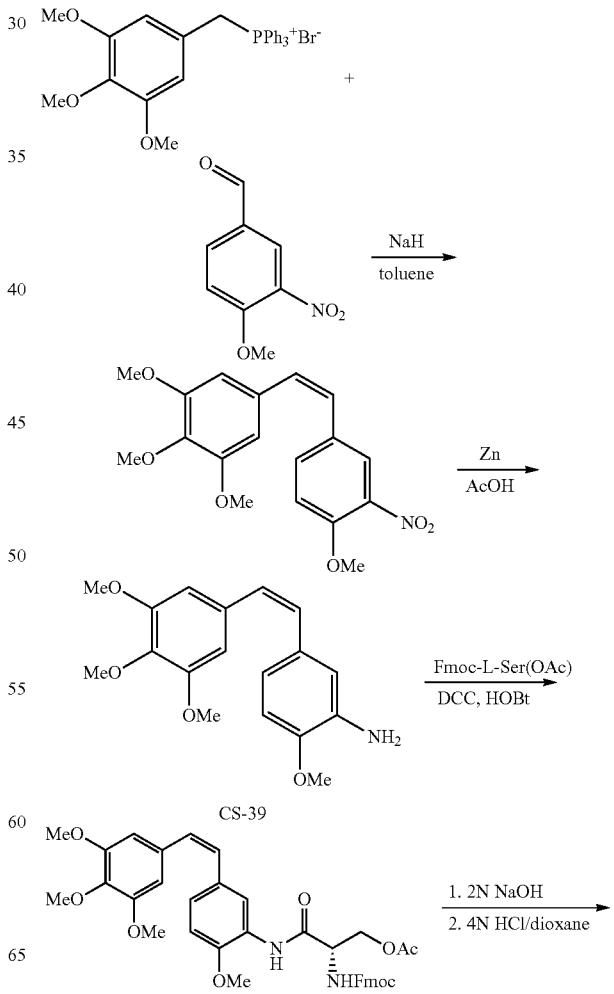

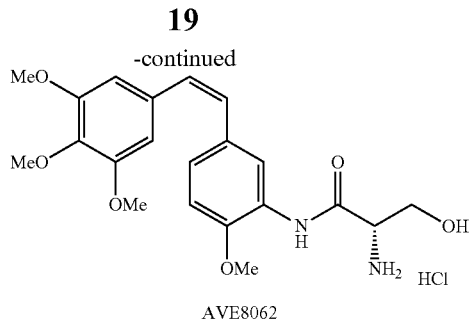

AVE8062

An additional stepwise synthesis of AVE8062 is described in detail below.

(Z)-1,2,3-trimethoxy-5-(4-methoxy-3-nitrostyryl) benzene

NaH (1.54 g, 64.2 mmol) was added into an oven-dried round-bottom reaction flask. Anhydrous CH2Cl2 (100 ml) and 3,4,5-trimethoxybenzyltriphenylphosphonium bromide (6.94 g, 13.3 mmol) were added to the reaction flask, and the reaction mixture was stirred for 1 h. The reaction mixture was cooled to −15° C., and 4-methoxy-3-nitrobenzaldehyde (2.01 g 11.1 mmol) was added to the reaction flask. The reaction mixture was stirred for 20 h while warming to ambient temperature under N2. Water (100 mL) was slowly added to the reaction, and the product was extracted with CH$_2$Cl$_2$ (3×100 mL). The organic phase was rinsed with brine, dried with Na$_2$SO$_4$, and concentrated under reduced pressure, and the residue was purified by flash column chromatography using a pre-packed 100 g silica column [solvent A: EtOAc; solvent B: hexanes; gradient: 10% A/90% B (1 CV), 10% A/90% B→70% A/30% B (10 CV), 70% A/30% B (5 CV); flow rate: 100 mL/min; monitored at 254 and 280 nm affording 3' CA4-nitro (1.51 g,

(S,Z)-2-((((9H-fluoren-9-yl)methoxy)carbonyl) amino)-3-((2-methoxy-5-(3,4,5-trimethoxystyryl) phenyl)amino)-3-oxopropyl acetate (47)

3' CA4-amine (0.11 g, 0.35 mmol) was dissolved in CH$_2$Cl$_2$ (10 mL), and then Fmoc-serine acetate (0.19 g, 0.52 mmol), T3P (0.62 mL, 1.0 mmol), and Et3N (0.073 mL, 0.52 mmol) were added. After stirring for 16 h at room temperature, water (10 mL) was added, and the reaction mixture was extracted with CH$_2$Cl$_2$ (3×10 ml). The combined organic phase was rinsed with brine, dried with Na$_2$SO$_4$, and concentrated under reduced pressure, and the residue was purified by flash column chromatography using a pre-packed 10 g silica column (solvent A: EtOAc; solvent B: hexanes; gradient: 12% A/88% B (1 CV), 12% A/88% B→100% A/0% B (10 CV), 100% A/0% B (2 CV); flow rate: 36 mL/min; monitored at 254 and 280 nm) affording the desired Fmoc-L-serinamide acetate (0.22 g, 0.32 mmol, 93%) as a white solid.

(S,Z)-2-amino-3-hydroxy-N-(2-methoxy-5-(3,4,5-trimethoxystyryl)phenyl)propanamide (3' CA4-L-serinamide)

To a well-stirred solution of Fmoc-L-serinamide acetate 47 (0.22 g, 0.32 mmol) in CH2Cl2/MeOH mixture (4 mL, 1:1 ratio), 2 N NaOH (2.00 eq.) was added. The reaction mixture was stirred for 2 h at room temperature under N$_2$. The solvent was evaporated under reduced pressure and sat. NaHCO$_3$ (10 mL) was added. The solution was extracted with CH$_2$Cl$_2$ (3×10 mL), and then the combined organic phase was rinsed with brine, dried with Na$_2$SO$_4$, and concentrated under reduced pressure. The residue was purified by preparative TLC [CH$_2$Cl$_2$/MeOH mixture (9:1 ratio)] to give the desired 3' CA4-L-serinamide prodrug (0.077 g, 0.19 mmol, 60%) as a yellow oil.

(S,Z)-2-amino-3-hydroxy-N-(2-methoxy-5-(3,4,5-trimethoxystyryl)phenyl)propanamide hydrochloride (AVE8062)

3' CA4-L-serinamide prodrug (0.027 g, 0.067 mmol) was dissolved in MeOH (0.50 mL), and 4 N HCl in dioxane (0.08 mL, 0.32 mmol) was added to the solution. After stirring for 5 min, the solvent was evaporated to dryness, and the residue was washed with diethyl ether (3×2 mL) to give the desired 3' CA4-L-serinamide prodrug salt AVE8062 (0.020 g, 0.046 mmol, 69%) as a colorless solid.

The Above Synthetic Method for AVE8062 is Shown Schematically Below

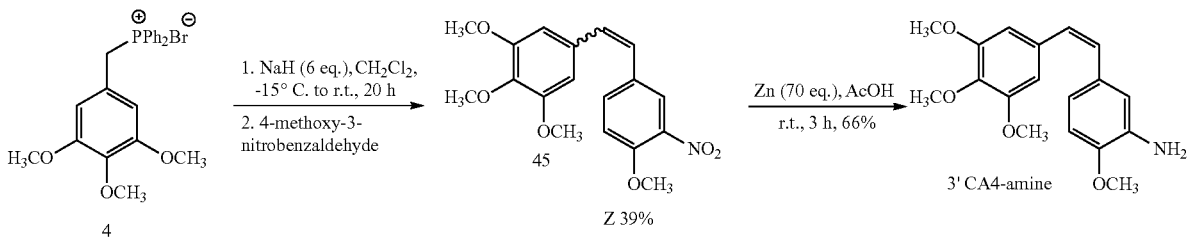

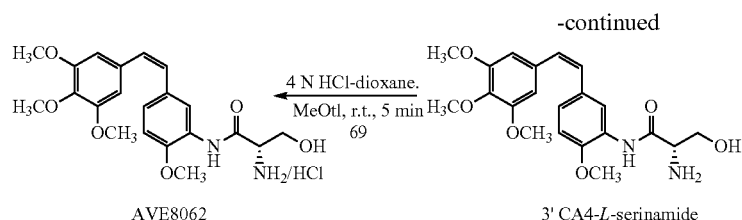
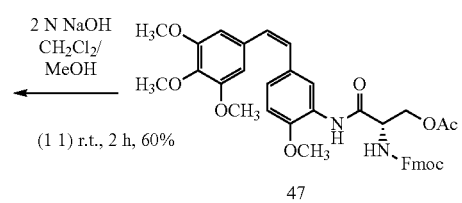

An additional synthetic method from (Ohsumi, K et al. Med. Chem. 1998, 41, 3022; Ohsumi, K et al. Anti-Cancer Drug Design 1999, 14, 539) is shown below

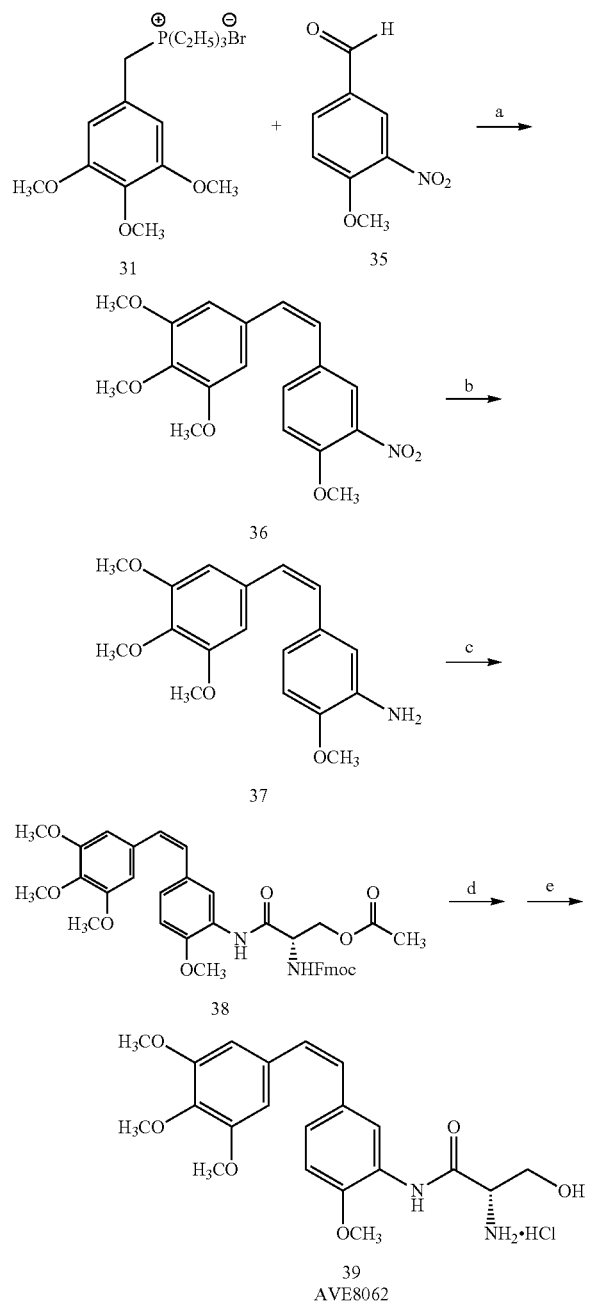

Reagents and conditions: (a) i—NaH toluene, rt; ii—separation of Z-isomer; (b) Zn, AcOH, rt; (c) Fmoc-L-Ser(Ac)—OH, DCC, HOBt/EH2O, DMF; (d) 2 N NaOH (aq); (e) 4 N HC/dioxane.

OXI-4503 (CA1P)

General

Oxi4503, the prodrug of the potent tubulin-binding agent CA1, behaves in a similar manner when compared to the CA4P regarding its dephosphorylation after administration. However, the preclinical evaluation of Oxi4503 shows that not only is it a much more potent agent than CA4P, but it can also induce tumor growth delays and regressions when used as a single agent.

Chemistry

OXi-4503 is the bis-phosphate prodrug of combretastatin A1 (CA1P). CA-1 and its prodrug disodium CA-1P-2,3-diphosphate (CA-1P, OXi4503) are cytotoxic against several human cancer lines and the cell lining of tumor vasculature. Combretastatin A1 (CA1) was isolated from *Combretum caffrum* and is a tubulin inhibitor similar to CA4. The instability of the 2,3-dihydroxyphenyl group, which can be easily oxidized to a 1,2-quinone, hindered the preclinical development of CA1. To overcome the instability problem as well as to increase the solubility of CA1, the phosphate of CA, together with a series of metal and ammonium cation salts, were synthesized. The tetra-sodium salt of CA1P was synthesized via reaction of CA1 with dibenzylphosphite in the presence of carbon tetrachloride, followed by deprotection with chlorotrimethylsilane, and treatment with sodium methoxide. The tetrasodium salt of CA1P was found to have the best aqueous solubility (120 mg/ml) and good activity against several cancer cell lines and was selected for preclinical studies. Synthetic scheme of CA1P from CA1 is shown above

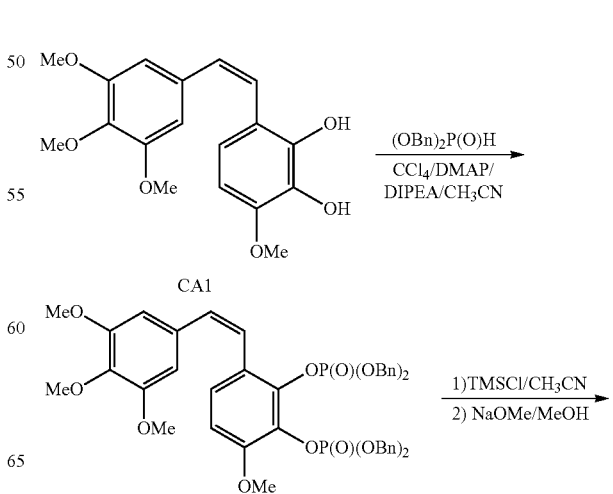

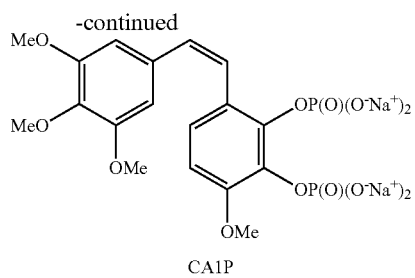

CA1P

Oxi4503 Synthesis: Tetrasodium Combretastatin A-1 2',3'-O-diphosphate (4)

To a solution of phosphate (3.2 g, 3.69 mmol) in acetonitrile (40 ml) under argon was added sodium iodide (2.2 g, 14.8 m mol, 4 eq). Before dropwise addition of chlorotrimethylsilane (1.9 ml, 14.9 mmol, 4 eq) the mixture was stirred for 2 min; 30 min later the reaction was terminated with 1% aq sodium thiosulfate (4 ml). Removal of the acetonitrile in vacuo afforded a crude mixture, which was dissolved in water-dichloromethane and washed with water (4×10 ml). Concentration (facilitated by toluene azeotrope) of the aqueous layer resulted in isolation of the crude phosporic acid intermediate which was then subjected to drying in high vacuum (1 h) and dissolved in dry methanol (10 ml under argon). Next, sodium methoxide (0.80 g, 14.8 mm ol, 4 eq) was added. The mixture was stirred (6 h) and additional methanol was added to effect dissolution.
After filtration of the solution, concentration of the methanol in vacuo led to an off-white solid, which was repreciptated from water-ethanol to yield a colorless powder.

An additional synthetic method for Oxi4503 from (Pettit, G. R.; Lippert, J. W., III Anti-Cancer Drug Design 2000, 15, 203) is shown below.

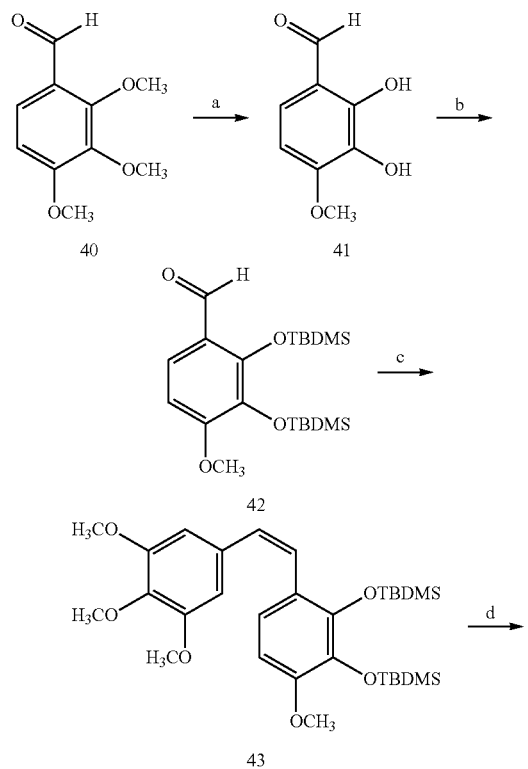

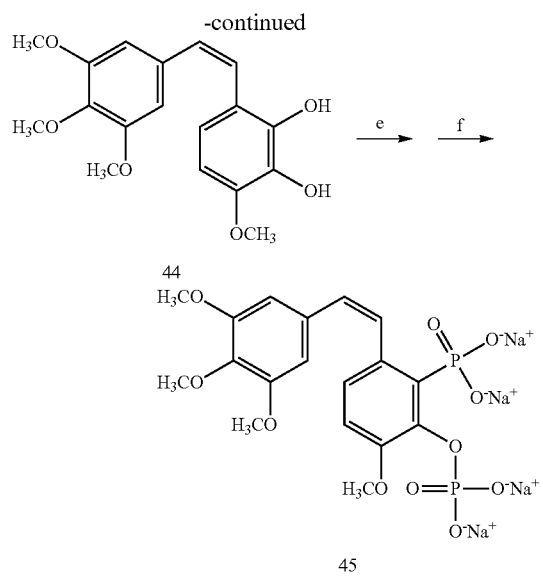

Reagents: (a) BCl3; (b) TBDMSCl; (c) separation of the Z-isomer; (d) 48% HBr/KF or TBAF; (e) (BnO)2P(O)H; (f) i ——TMSCl, NaI; ii ——NaOCH3

Disodium CA-4-3-O-phosphate (CA-4P; Zybrestat)

This agent has moved into clinical trials Clinical studies aiming to assess the dose-limiting toxicity and anti-tumor effectiveness of CA-4P showed maximum tolerated dose in the range 60-68 mg/m$^2$. In clinical trials, a significant reduction in tumor blood flow was observed at doses equal to or below the maximum tolerated dose. In solid tumors, CA-4P exerted a therapeutic effect on the inner part of the tumor tissue, leaving a rim of viable tumor cells at the periphery. Therefore, CA-4P is proposed in combination with other therapies that are more effective at treatment of the outer tumor region.

The structures of three combretastatin prodrugs useful in this invention include but are not limited to those shown below.

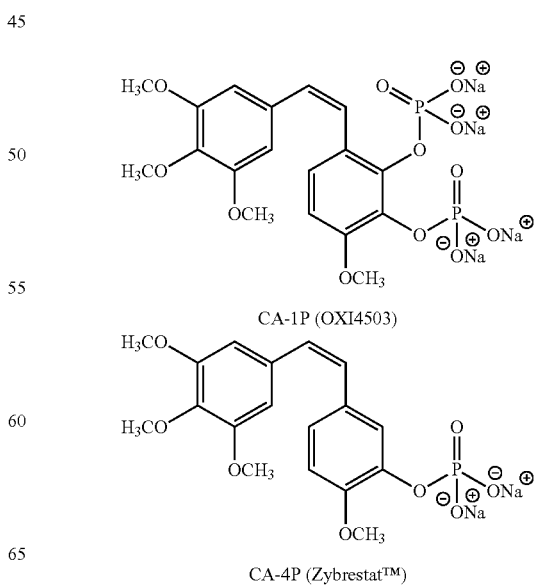

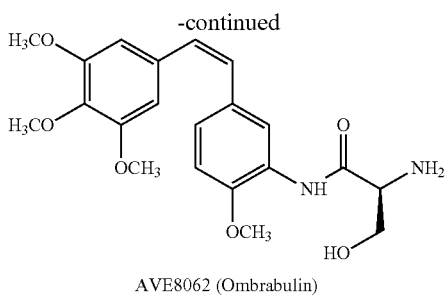

AVE8062 (Ombrabulin)

Compounds of the present invention are prepared from commonly available compounds using procedures known to those skilled in the art, including any one or more of the following conditions without limitation: Within the scope of this text, only a readily removable group that is not a constituent of the particular desired end product of the compounds of the present invention is designated a "protecting group unless the context indicates otherwise. The protection of functional groups by such protecting groups, the protecting groups themselves, and their cleavage reactions are described for example in standard reference works, such as e.g., Science of Synthesis: Houben Weyl Methods of Molecular Transformation. Georg Thieme Verlag, Stuttgart, Germany. 2005.41627 pp. (URL: http://www.science-of-synthesis.com (Electronic Version, 48 Volumes)); J. F. W. McOmie, "Protective Groups in Organic Chemistry", Plenum Press, London. And New York 1973, in T. W. Greene and P. G. M. Wuts, "Protective Groups in Organic Synthesis". Third edition, Wiley, New York 1999, in "The Peptides': Volume 3 (editors: E. Gross and J. Meienhofer), Academic Press, London and New York 1981, in "Methodender organischen Chemie' (Methods of Organic Chemistry), Houben Weyl, 4th edition, Volume 15/I, Georg Thieme Verlag. Stuttgart 1974, in H.-D. Jakubke and H. Jeschkeit, Aminosauren, Peptide, Proteine (Amino acids, Peptides, Proteins), VerlagChemie, Weinheim, Deerfield Beach, and Basel 1982, and in Jochen Lehmann, Chemie der Kohlenhydrate: Monosaccharide und Derivate (Chemistry of Carbohydrates. Monosaccharides and Derivatives), Georg Thieme Verlag, Stuttgart 1974. A characteristic of protecting groups is that they can be removed readily (i.e., without the occurrence of undesired secondary reactions) for example by Sol Volysis, reduction, photolysis or alternatively under physiological conditions (e.g., by enzymatic cleavage).

Acid addition salts of the compounds of the invention are most suitably formed from pharmaceutically acceptable acids and include for example those formed with inorganic acids e.g. hydrochloric, hydrobromic, sulphuric or phosphoric acids and organic acids e.g. succinic, malaeic, acetic or fumaric acid. Other non-pharmaceutically acceptable salts e.g. oxalates can be used for example in the isolation of the compounds of the invention, for laboratory use, or for subsequent conversion to a pharmaceutically acceptable acid addition salt. Also included within the scope of the invention are solvates and hydrates of the invention.

The conversion of a given compound salt to a desired compound salt is achieved by applying standard techniques, in which an aqueous solution of the given salt is treated with a solution of base e.g. sodium carbonate or potassium hydroxide, to liberate the free base which is then extracted into an appropriate solvent, such as ether. The free base is then separated from the aqueous portion, dried, and treated with the requisite acid to give the desired salt.

In vivo hydrolyzable esters or amides of certain compounds of the invention can be formed by treating those compounds having a free hydroxy or amino functionality with the acid chloride of the desired ester in the presence of a base in an inert solvent such as methylene chloride or chloroform. Suitable bases include triethylamine or pyridine. Conversely, compounds of the invention having a free carboxy group can be esterified using standard conditions which can include activation followed by treatment with the desired alcohol in the presence of a suitable base.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzene sulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methane sulphonate derived from methane sulphonic acid, the naphthalene-2-Sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-Sulphonate derived from p-toluene sulphonic acid, and the like. Particularly preferred salts are sodium, lysine and arginine salts of the compounds of the invention. Such salts can be formed by procedures well known and described in the art.

Other acids such as oxalic acid, which cannot be considered pharmaceutically acceptable, can be useful in the preparation of salts useful as intermediates in obtaining a chemical compound of the invention and its pharmaceutically acceptable acid addition salt. Metal salts of a chemical compound of the invention include alkali metal salts. Such as the sodium salt of a chemical compound of the invention containing a carboxy group. Mixtures of isomers obtainable according to the invention can be separated in a manner known into the individual isomers; diastereoisomers can be separated, for example, by partitioning between polyphasic solvent mixtures, recrystallisation and/or chromatographic separation, for example over silica gel or by, e.g., medium pressure liquid chromatography over a reversed phase column, and racemates can be separated, for example, by the formation of salts with optically pure salt-forming reagents and separation of the mixture of diastereoisomers so obtainable, for example by means of fractional crystallization, or by chromatography over optically active column materials. Intermediates and final products can be worked up and/or purified according to standard methods, e.g., using chromatographic methods, distribution methods, (re-) crystallization, and the like.

Flavone Acetic Acid (FAA) Derivatives and 5,6-dimethylanthenone-4-acetic Acid (DMXAA)

An additional class of small molecule vascular disrupting agents is the flavone acetic acid (FAA) derivatives. Flavonoids have a unique mechanism of action and are believed to exert their effects primarily by inducing localized release of TNF-α and other cytokines within tumor tissue. A more potent analogue of FAA, called 5,6-dimethylxanthenone-4-acetic acid (DMXAA), has been extensively studied. Treatment of tumor-bearing mice with DMXAA results in a rapid reduction in tumor blood flow followed by tumor necrosis with only a rim
of viable tumor tissue remaining by 24 hours. DMXAA selectively arrests blood flow in murine tumors within 30 min of administration and tumor
scintigraphic imaging of hypoxic tumor tissue from mice treated with DMXAA showed the onset of hypoxia, consistent with inhibition of blood flow. In addition, DMXAA induces early changes in tumor vascular endothelial cells that are indicative of apoptosis. DMXAA also causes a dose-dependent increase in plasma concentrations of 5HT and its hepatic metabolite 5-hydroxyindole-3-acetic
acid (5HIAA), suggesting that 5HT is released by platelets in response to vascular damage. Moreover, DMXAA induces synthesis of tumor necrosis factor (TNF) in plasma and in tumor tissue and induces the synthesis of nitric oxide. In mice DMXAA has been shown to activate the STING network for interferon activation. The structure of DMXAA is shown below. Synthesis of DMXAA is described by Atwell G J et al. Eur J Med Chem. 2002 October; 37(10): 825-8. Structures and synthesis of the newer C7 derivatives of DMXAA with ability to activate the human STING complex are given in Hwang J et al. Org. Biomol. Chem., 2019, 17, 1869-1874. In a phase 1 clinical trial DMXAA doses of 300, 600, 1,200, 1,800, 2,400, and 3,000 mg/m$^2$ were assessed and a dose of 1200 mg/m$^2$ was selected for further study (McKeage M J et al. Clin Cancer Res 2006; 12(6) Mar. 15, 2006).

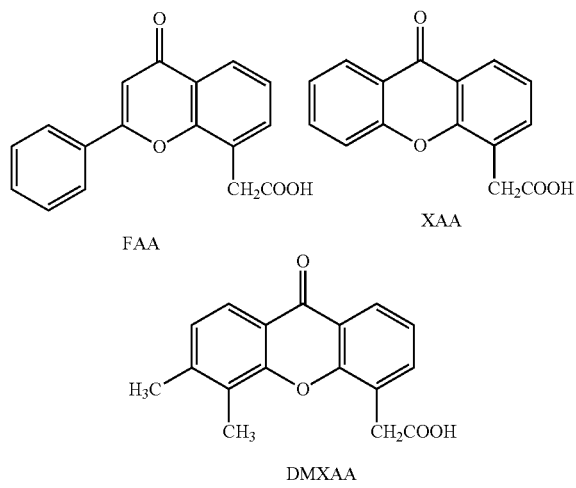

FAA

XAA

DMXAA

Metes and Bounds of Combretastatins in the Instant Invention: Form, Schedules, Dose Range As explained above, embodiments of the present invention include a pharmaceutical compositions that modulates growth of metastasis of tumors, particularly solid tumors, using a pharmaceutical composition of the present invention, along with methods of modulating tumor growth or metastasis, for example, with a pharmaceutical composition of the present invention. The present invention provides, in part, methods for producing an enhanced antitumor effect employing a combination of agents. Aspects, the methods of the invention comprise the administration (e.g., sequential administration or co-administration) of a Vascular Disrupting Agent and sickle cells and radiation. The methods of the present invention provide advantages such as greater overall therapeutic efficacy of VDA therapy, for example, by preventing tumor regrowth. Further, where a tumor to be treated is not optimally responsive (e.g. resistant) to treatment with a Vascular Disrupting Agent, use of the present combination therapy methods can nonetheless provide effective treatment. In one aspect, the invention provides a method for producing an anti-tumor effect in a patient suffering from a cancer or tumor, the method comprising administering to the patient a VDA and sickle cells and radiation.

The VDA is administered 4-48 hours after radiation treatment to the tumor. It is also administered together with or 30 minutes to 48 hours before sickle cell infusion. In a preferred embodiment, the VDA is administered 24 hours after radiation 1 hour before sickle cell infusion to produce a potentiated antitumor effect. In another embodiment the VDA and sickle cells may be administered sequentially in any order to produce a potentiated antitumor effect. In a preferred embodiment, sickle cells are is sequentially administered in any order with an effective amount of a VDA (e.g., a combretastatin). In a still more preferred embodiment, combretastatin A-4 phosphate (CA4P) or combretastatin A-1 diphosphate (CA1P) is sequentially or simultaneously administered in any order with an effective amount of radiation and sickle cells. Preferably, radiation treatment precedes the administration of combretastatin and sickle cells by 4-48 hours.

In another aspect, the invention provides a pharmaceutical composition comprising a VDA (e.g., a combretastatin) and sickle cells plus sublethal radiation. As indicated sickle cells or its variants as described above are useful. In a particular embodiment, the dosages of sickle cells or its variants are given above and under Pharmaceutical Delivery.

In a phase I safety, pharmacokinetic and pharmacodynamic evaluation of the vascular disrupting agent Ombrabulin (AVE8062) in patients with advanced solid tumors the recommended schedule for single-agent Ombrabulin is 50 mg/m$^2$ every 3 weeks (Sessa C et al., Clin Cancer Res; 19(17); 4832-42) 2014). A dosage range of 20-70 mg/m$^2$ every 2-5 weeks is considered to produce anti-tumor effects.

In a phase I safety, pharmacokinetic and pharmacodynamic evaluation of the vascular disrupting agent Oxi4503 in patients with advanced solid tumors the maximum tolerated dose was 8.5 mg/m$^2$ but escalation to 14 mg/m$^2$ was possible. As a tumor response was seen at 14 mg/m$^2$ and maximum tumor perfusion reductions were seen at doses of 11 mg/m$^2$ or higher, the recommended phase II dose is from 11 to 14 mg/m$^2$ every three weeks (Sessa C et al., *Clin Cancer Res;* 18(5); 1415-25 (2012).

Radiation Therapy

Radiation therapy: includes but is not limited to X-rays or gamma rays which are delivered from either an externally supplied source such as a beam or by implantation of small radioactive sources. Historically, the three main divisions of radiation therapy are: external beam radiation therapy (EBRT or XRT) or teletherapy; brachytherapy or sealed source radiation therapy; and systemic radioisotope therapy or unsealed source radiotherapy Radiation therapies which are suitable for use in the combination treatments described herein, include the use of a) external beam radiation; and b) a radiopharmaceutical agent which comprises a radiation-emitting radioisotope.

External Beam Radiation

External beam radiation therapy for the treatment of cancer uses a radiation source that is external to the patient, typically either a radioisotope, Such as Co, Cs, or a high energy x-ray source such as a linear accelerator. The external source produces a collimated beam directed into the patient to the tumor site. External-source radiation therapy avoids some of the problems of internal-source radiation therapy, but it irradiates a significant volume of non-tumorous or healthy tissue in the path of the radiation beam along with the tumorous tissue.

The adverse effect of irradiating healthy tissue can be reduced, while maintaining a given dose of radiation in the tumorous tissue, by projecting the external radiation beam into the patient at a variety of angles with the beams converging on the tumor site. The particular volume elements of healthy tissue along the path of the radiation beam change, reducing the total dose to healthy tissue during the entire treatment.

The irradiation of healthy tissue also can be reduced by tightly collimating the radiation beam to the general cross section of the tumor taken perpendicular to the axis of the radiation beam. Numerous systems exist for producing such a circumferential collimation, some of which use multiple sliding Shutters which, piecewise, can generate a radio-opaque mask of arbitrary outline.

Radiopharmaceutical Agents

A "radiopharmaceutical agent", as defined herein, refers to a pharmaceutical agent which contains at least one radiation-emitting radioisotope. Radiopharmaceutical agents are routinely used in nuclear medicine for the diagnosis and/or therapy of various diseases. The radiolabeled pharmaceutical agent, for example, a radiolabeled antibody, contains a radioisotope (RI) which serves as the radiation source. As contemplated herein, the term "radioisotope' includes metallic and non-metallic radioisotopes. The radioisotope is chosen based on the medical application of the radiolabeled pharmaceutical agents. When the radioisotope is a metallic radioisotope, a chelator is typically employed to bind the metallic radioisotope to the rest of the molecule. When the radioisotope is a non-metallic radioisotope, the non-metallic radioisotope is typically linked directly, or via a linker, to the rest of the molecule.

As used herein, a "metallic radioisotope' is any suitable metallic radioisotope useful in a therapeutic or diagnostic procedure in vivo or in vitro. Identifying the most appropriate isotope for radiotherapy requires weighing a variety of factors. These include tumor uptake and retention, blood clearance, rate of radiation delivery, half-life and specific activity of the radioisotope, and the feasibility of large-scale production of the radioisotope in an economical fashion. The key point for a therapeutic radiopharmaceutical is to deliver the requisite amount of radiation dose to the tumor cells and to achieve a cytotoxic or tumoricidal effect while not causing unmanageable side-effects. It is preferred that the physical half-life of the therapeutic radioisotope be similar to the biological half-life of the radiopharmaceutical at the tumor site. For example, if the half-life of the radioisotope is too short, much of the decay will have occurred before the radiopharmaceutical has reached maximum target/background ratio. On the other hand, too long a half-life would cause unnecessary radiation dose to normal tissues. Ideally, the radioisotope should have a long enough half-life to attain a minimum dose rate and to irradiate all the cells during the most radiation sensitive phases of the cell cycle. In addition, the half-life of a radioisotope must be long enough to allow adequate time for manufacturing, release, and transportation.

The target receptor sites in tumors are typically limited in number. As such it is preferred that the radioisotope have high specific activity. The specific activity depends primarily on the production method.

The type of radiation that is suitable for use in the methods of the present invention can vary. For example, radiation can be electromagnetic or particulate in nature. Electromagnetic radiation useful in the practice of this invention includes but is not limited to x-rays and gamma rays. Particulate radiation useful in the practice of this invention includes, but is not limited to, electron beams (beta particles), protons beams, neutron beams, alpha particles, and negative pi mesons. The radiation can be delivered using conventional radiological treatment apparatus and methods, and by intraoperative and Stereotactic methods. Additional discussion regarding radiation treatments suitable for use in the practice of this invention can be found throughout Steven A. Leibel et al., Textbook of Radiation Oncology (1998) (publ. W. B. Saunders Company), and particularly in Chapters 13 and 14. Radiation can also be delivered by other methods such as targeted delivery, for example by radioactive "seeds," or by systemic delivery of targeted radioactive conjugates. J. Padawer et al., Int. J. Radiat. Oncol. Biol. Phys. 7:347-357 (1981). Other radiation delivery methods can be used in the practice of this invention.

For tumor therapy, both C. and B-particle emitters have been investigated. Alpha particles are particularly good cytotoxic agents because they dissipate a large amount of energy within one or two cell diameters. The β-particle emitters have relatively long penetration range (2-12 mm in the tissue) depending on the energy level. The long-range penetration is particularly important for Solid tumors that have heterogeneous blood flow and/or receptor expression. The β-particle emitters yield a more homogeneous dose distribution even when they are heterogeneously distributed within the target tissue.

Modes and Doses of Administration

The methods of the present invention comprise administering to a patient in need thereof a first amount of radiation in a first treatment procedure, and a second amount or dose of sickle cells and combretastatin a second treatment procedure. The first and second amounts together comprise a therapeutically effective amount.

Administration of External Beam Radiation

For administration of external beam radiation, the amount can be at least about 1 Gray (Gy) fractions at least once every other day to a treatment volume. In a particular embodiment, the radiation is administered in at least about 2 Gray (Gy) fractions at least once per day to a treatment volume. In another particular embodiment, the radiation is administered in at least about 2 Gray (Gy) fractions at least once per day to a treatment volume for five consecutive days per week. In another particular embodiment, radiation is administered in 10 Gy fractions every other day, three times per week to a treatment volume. In another particular embodiment, a total of at least about 20 Gy is administered to a patient in need thereof. In another particular embodiment, at least about 30 Gy is administered to a patient in need thereof. In another particular embodiment, at least about 40 Gy is administered to a patient in need thereof. Typically, the patient receives external beam therapy four or five times a week. An entire course of treatment usually lasts from one to seven weeks depending on the type of cancer and the goal of treatment. For example, a patient can receive a dose of 2 Gy/day over 30 days. In the instant invention, the radiation to the tumor is delivered 4-24 hours before sickle cells infusion and VDA injection, The combined regimen can be delivered at intervals of 3-30 days. The dose of radiation per treatment is generally 10-20 Gy. The frequency of radiation treatment is governed by the rate of reduction of the tumor mass and is repeated once the tumor regression has stabilized or shows signs of regrowth. In another protocol the treatment is given on a fixed schedule of 7-10 days until a dose of 60 Gy of radiation has been delivered to the tumor.

Administration of Radiopharmaceutical Agent

There are several methods for administration of a radiopharmaceutical agent. For example, the radiopharmaceutical agent can be administered by targeted delivery or by Systemic delivery of targeted radioactive conjugates, Such as a radiolabeled antibody, a radiolabeled peptide and a Liposome delivery System.

In one particular embodiment of targeted delivery, the radiolabeled pharmaceutical agent can be a radiolabeled antibody. See, for example, Ballangrud A. M., et al. Cancer Res., 2001; 61:2008-2014 and Goldenberg, D M J. Nucl. Med., 2002; 43(5):693-713, the contents of which are incorporated by reference herein.

In another particular embodiment of targeted delivery, the radiopharmaceutical agent can be administered in the form of liposome delivery Systems, Such as small unilamellar vesicles, large unilamellar vesicles and multilamellar vesicles. Liposomes can be formed from a variety of phospholipids, Such as cholesterol, stearylamine or phosphatidylcholines. See, for example, Emfietzoglou D, Kostarelos K, SgouroS G. An analytical dosimetry Study for the use of radionuclide-liposome conjugates in internal radiotherapy. J Nucl Med 2001; 42:499-504, the contents of which are incorporated by reference herein.

0237. In yet another embodiment of targeted delivery, the radiolabeled pharmaceutical agent can be a radiolabeled peptide. See, for example, Weiner R E, Thakur M L. Radiolabeled peptides in the diagnosis and therapy of oncological diseases. Appl Radiat Isot 2002 November; 57(5): 749 63, the contents of which are incorporated by reference herein. In addition to targeted delivery, Brachytherapy can be used to deliver the radiopharmaceutical agent to the target site.

Brachytherapy is a technique that puts the radiation sources as close as possible to the tumor site. Often the source is inserted directly into the tumor. The radioactive sources can be in the form of wires, Seeds or rods. Generally, cesium, iridium or iodine are used. There a two types of brachytherapy: intercavitary treatment and interstitial treatment. In intracavitary treatment, containers that hold radioactive Sources are put in or near the tumor. The sources are put into the body cavities. In interstitial treatment the radioactive sources alone are put into the tumor. These radioactive Sources can stay in the patient permanently. Most often, the radioactive sources are removed from the patient after several days. The radioactive sources are in containers. The amount of radiation necessary can be determined by one of skill in the art based on known doses for a particular type of cancer. See, for example, Cancer Medicine 5" ed., Edited by R. C. Bast et al., July 2000, B C Decker, the entire content of which is hereby incorporated by reference. In a particular embodiment, the radiation can be administered in amount effective to cause the arrest or regression of the cancer when the radiation is administered with the combretastatin or combretastatin prodrugs or other VDAs plus sickle cells or sickle cell variant cells.

Combination Administration

The radiation can be administered prior to onset of treatment with the combretastatin or sickle cells, at the same time as combretastatin or sickle cells or following treatment with combretastatin and sickle cells. In addition, radiation treatment can be administered during the period of combretastatin and sickle cell administration but does not need to occur over the entire combretastatin and sickle cell administration treatment period.

Dose and Fractionation

While the mouse model uses external beam radiation to the tumor in doses of 10-15 Gy, human solid tumors are usually treated with 60-80 Gy. However, hypofractionated radiation schedules allows a window for tumor treatment with sublethal doses over a defined interval. Hence tumor treatment can be initiated in the doses used in the mouse model and the subsequent dosage adjusted over time in accord with the tumor response. Typical doses vary significantly by cancer type from 2.2 Gy/fraction to 20 Gy/fraction, The total dose is fractionated (spread out over time) for several important reasons. Fractionation allows normal cells time to recover, while tumor cells are generally less efficient in repair between fractions. Fractionation also allows tumor cells that were in a relatively radio-resistant phase of the cell cycle during one treatment to cycle into a sensitive phase of the cycle before the next fraction is given. Similarly, tumor cells that were chronically or acutely hypoxic (and therefore more radioresistant) may reoxygenate between fractions, improving the tumor cell kill.[38]

The amount of radiation used in photon radiation therapy is measured in grays (Gy), and varies depending on the type and stage of cancer being treated. For curative cases, the typical dose for a solid epithelial tumor ranges from 60 to 80 Gy, while lymphomas are treated with 20 to 40 Gy. Preventive (adjuvant) doses are typically around 45-60 Gy in 1.8-2 Gy fractions (for breast, head, and neck cancers.) Many other factors are considered by radiation oncologists when selecting a dose, including whether the patient is receiving chemotherapy, patient comorbidities, whether radiation therapy is being administered before or after surgery, and the degree of success of surgery. Delivery parameters of a prescribed dose are determined during treatment planning (part of dosimetry).

Fractionation regimens are individualized between different radiation therapy centers and even between individual doctors. In North America, Australia, and Europe, the typical fractionation schedule for adults is 1.8 to 2 Gy per day, five days a week. In some cancer types, prolongation of the fraction schedule over too long can allow for the tumor to begin repopulating, and for these tumor types, including head-and-neck and cervical squamous cell cancers, radiation treatment is preferably completed within a certain amount of time. For children, a typical fraction size may be 1.5 to 1.8 Gy per day, as smaller fraction sizes are associated with reduced incidence and severity of late-onset side effects in normal tissues.

In some cases, two fractions per day are used near the end of a course of treatment. This schedule, known as a concomitant boost regimen or hyperfractionation, is used on tumors that regenerate more quickly when they are smaller. In particular, tumors in the head-and-neck demonstrate this behavior.

In the instant invention, a preferred regimen is that radiation to the tumor is given 4-24 hours before administration of sickle cells and VDA. The preferred initial dose of radiation is 10 Gy delivered by external beam or stereotactically. This dose is repeated in 7 to 10 days together with repeat administration of sickle cells and VDA. The same regimen may be repeated thereafter at 2-6-week intervals until a total dose of 60 Gy is administered to the tumor. An anti-tumor response may be achieved before the full dose of radiation is administered. The initial and repeated dose of radiation can be varied depending on the susceptibility of a given tumor type.

One fractionation schedule that is increasingly being used and continues to be studied is hypofractionation. Here the total dose of radiation is divided with typical doses varying by cancer type, from 2.2 Gy/fraction to 20 Gy/fraction. The latter is typical of stereotactic treatments (stereotactic ablative body radiotherapy, or SABR—also known as SBRT, or stereotactic body radiotherapy) for subcranial lesions, or SRS (stereotactic radiosurgery) for intracranial lesions. The rationale of hypofractionation is to reduce the probability of local recurrence by denying clonogenic cells the time required to reproduce and to exploit the radiosensitivity of some tumors. In particular, stereotactic treatments are intended to destroy clonogenic cells by delivery of a dose intended to destroy clonogenic cells directly, rather than to interrupt the process of clonogenic cell division repeatedly (apoptosis), as in routine radiotherapy. Methionine Depletion We contemplate the use of Combretastatin A-1 diphosphate (CA1P) for treatment cancer in combination with SSRBC infusions, radiation and methionine depletion therapy. Methionine is an essential amino acid with a multitude of functions. It is prominent in protein translation, since it is the N-terminal amino acid of most mammalian proteins. Methionine is required for polyamine synthesis. It is also requisite for polyamine function during nuclear and cell division. Moreover, methionine is converted to S-adenosylmethionine (SAM) by a family of conserved methionine adenosyltransferase. SAM is the major source of methyl groups needed for methylation of nucleic acids, proteins, and the cap structure of mRNAs, as well as biosynthesis of phospholipids and glutathione. In addition, because it is the cofactor for chromatin methylation, SAM is an important metabolite for the establishment and maintenance of epigenetic marks. Transient pharmacological inhibition of methionine cycle enzymes has been shown to result in loss of tumorigenic potential. This is largely attributed to alterations in cellular methylation that produce depletion of SAM.

Combining dietary methionine deficiency with inhibition of SAM biosynthesis inhibits mammary tumor growth and lung metastases more robustly than methionine restriction alone. Indeed, dietary methionine restriction induced the expression of MAT2A in mammary tumors, providing additional mechanistic insights into the enhanced efficacy of dual targeting of SAM biosynthesis. MAT2A is often aberrantly expressed in human tumors in response to HIF-1α, IGF-1, Nrf2 and EGF and promotes cell growth and drug resistance. Methionine stress activates MAT2A gene expression in tumor cells, thereby "priming" them to respond to MAT2A inhibition by undergoing apoptosis or differentiation. Silencing MAT2A inhibits proliferation and induces apoptosis in carcinoma cells. Collectively, these findings point to MAT2A as a promising therapeutic target in cancer.

Methionine restriction alone has minimal anti-tumor effect alone but is powerful when combined with chemotherapy and some biologics. The effect on tumor growth in most cases has not been complete with evident tumor re-growth beginning on day 8 after starting treatment. This has prompted a search for regimens that could better interact with methionine restriction. Recent studies have shown that radiation/Oxi4503/SSRBCs treatment as described below induces substantial tumor regression by inducing disseminated tumor vaso-occlusion/infarction involving up to 95% of the tumor area. The treated tumors exhibited severe hypoxia and reduced tumor cell proliferation. We reasoned that the hypoxic/irradiated TME would render tumor cells more sensitive to the tumoricidal effect of methionine restriction (MR). More specifically, the ability of MR to inhibit cell cycle activity could be augmented in the TME conditioned by the regimen. To obtain more comprehensive methionine depletion a methionine deficient diet together with FIDAS-5 a SAM inhibitor was used as described below. By combining radiation/Oxi4503/SSRBCs treatment with MR in mice with established LLC we found that this combinatorial treatment resulted in sustained tumor regression for 30 days. This was corroborated histopathologically by the presence of both tumor necrosis and apoptosis in the TME.

Methionine Depletion Produced by Methionine Deficient Diet and FIDAS-5

Therapeutic methionine depletion is effected by using a methionine deficient diet together with FIDAS-5. The methionine deficient diet used to induce methionine deficiency is shown below.

| Modified L-Amino Acid Defined Lombardi Choline & Methionine Deficient Diet with 1.7 g/kg of DL-Homocystine | |
|---|---|
| L-Alanine | 5.1 |
| L-Arginine | 12.7 |
| L-Aspartic Acid | 15.8 |
| L-Cystine | 3.7 |
| L-Glutamic Acid | 28.9 |
| Glycine | 6.2 |
| L-Histidine | 3.4 |
| L-Isolecine | 6.1 |
| L-Leucine | 10.5 |
| L-Lysince-HCl | 9.1 |
| L-Methionine | 0 |
| L-Phenylalanine | 7.3 |
| L-Proline | 7.6 |
| L-Serine | 7.2 |
| L-Threonine | 4.6 |
| L-Tryptophan | 1.8 |
| L-Tyrosine | 5.7 |
| L-Valine | 6.3 |
| DL-Homocystine | 1.7 |
| Totals | 143.7 Gm/Kg (574.8 Kcal/Gm) |

| Ingredient | kcal/gm | gm/Kg | kcal/gm |
|---|---|---|---|
| Cornstarch | 3.6 | 100 | 360 |
| Dextrin | 3.63 | 100 | 363 |
| Sucrose | 4 | 413 | 1652.00 |
| Cellulose Mircrocrystalline | 0 | 44 | 0 |
| Corn Oil | 9 | 50 | 450 |
| Primex | 9 | 100 | 900 |
| Salt Mix #200000 | 0.47 | 35 | 16.45 |
| Sodium Bicarbonate | 0 | 4.3 | 0 |
| Vitamin Mix #300050 | 3.92 | 10 | 39.2 |
| Choline Bitartrate | 0 | 0 | 0 |
| other total | | 856.30 | 3780.65 |
| grand total | | 1000.00 | 4355.45 |

Methionine depletion was further enhanced by the addition of FIDAS-5. FIDAS-5, a cell-permeable fluorinated N,N-dialkylaminostilbene (FIDAS) analogue of FIDAS-3 that is >2-fold more potent than FIDAS-3 in inhibiting MAT2A-catalyzed SAM (S-adenosylmethionine) synthesis both in cell-free ($IC_{50}$=2.1 µM with FIDAS-5 vs. 4.9 µM with FIDAS-3; [L-Met]=[ATP]=1 mM, [MAT2A]=10 µg/mL; 20 min FIDAS preincubation prior to 30 min reaction) and cell-based (64% and 56% decrease of SAM and SAH level, respectively, in LS174T cells after 36 h treatment with either 3 µM FIDAS-5 or 10 µM FIDAS-3) assays. FIDAS-5 at 3 µM is shown to completely inhibit the proliferation of LS174T CRC (colorectal cancer) for up to 7 d in vitro and, when administered orally, effectively suppress HT29 CRC tumor expansion in mice in vivo (by 58% on d 18 post HT29 xenograft; 20 mg/kg/day starting d 4). Computer-aided in silico modeling predicts that FIDAS-3 & -5 target SAM-binding pocket at the interface of MAT2A dimer and in vitro binding studies reveals FIDAS-3 effectively competes against SAM for MAT2A binding.

A cell permeable fluorinated N,N-dialkylaminostilbene (FIDAS) analogue of FIDAS-3 that competes against SAM for MAT2A binding and is >2-fold more potent than FIDAS-3 in inhibiting MAT2A-catalyzed SAM synthesis both in cell-free assays ($IC_{50}$=2.1 µM) and in –LS174T colorectal cancer (CRC) cultures (3 µM). FIDAS-5 at 3 µM is shown to completely inhibit the proliferation of LS174T for up to 7 d in vitro and effectively suppress HT29 CRC tumor expansion in mice in vivo (20 mg/kg/day p.o.).

Examples of synthesis of fluorinated N,N-Dialkylaminostilbenes including FIDAS-5 are provided in Zhang W et al. Med Chem. 2011 Mar. 10; 54(5): 1288-1297. doi:10.1021/jm101248v.

Multi-Component Combination Therapy: Radiation+Combretastatin+Sickle Cells

The combination therapy methods and pharmaceutical compositions of the invention comprise a VDA including but not limited to combretastatin and combretastatin prodrug (collectively combretastatins) with sickle cell or sickle cell variant or sickle cell erythroid precursor infusion(s) (collectively sickle cells) and radiation as explained above. These agents can also be effectively combined with measures that deplete methionine in the tumor bearing host. Preferably radiation is administered 4-48 hours before administration of sickle cell infusion and combretastain prodrug administration. Sickle cell infusions and combretastatin prodrug infusions may be delivered simultaneously or sequentially within 4 hours of each other in either order. Preferentially, combretastatin prodrugs are delivered in advance of sickle cells by 30 minutes to 4 hours.

Pharmaceutical Compositions

As explained above, the present methods can, for example, be carried out using a single pharmaceutical composition comprising both a VDA and sickle cells when administration is to be simultaneous or sequential.

Pharmaceutical Compositions and Administration of Sickle Cells, Sickle Cell Variant Cells and Sickle Cell Precursors Sickle cells as used here includes sickle cells, sickle cell variant cells, nucleated sickle cell precursors and progenitor cells may be administered parenterally preferably intravenously by infusion or injection. The pharmaceutical compositions of the present invention will generally comprise an effective amount of sickled erythrocytes dissolved or dispersed in a pharmaceutically acceptable aqueous medium. One or more administrations may be employed the response of the tumor to the drug. Administration may be by syringe, catheter or other convenient means allowing for introduction of a flow-able composition. Administration may be every three days, weekly, or less frequent, such as biweekly or at monthly intervals.

The phrases "pharmaceutically or pharmacologically acceptable" refer to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. For human administration, preparations should meet sterility, pyrogenicity, general safety and purity standards as required by U. S. Food and Drug Administration. Supplementary active ingredients can also be incorporated into the compositions.

"Unit dosage" formulations are those containing a dose or sub-dose of the administered ingredient adapted for a particular timed delivery. For example, exemplary "unit dosage" formulations are those containing a daily dose or unit or daily sub-dose or a weekly dose or unit or weekly sub-dose and the like.

Injectable Formulations

The sickle cells compositions of the present invention are preferably formulated for parenteral administration, e.g., introduction by injection, infusion. They are preferably administered intravenously or intraarterially. Means for preparing aqueous compositions that contain the sickle cells compositions are known to those of skill in the art in light of the present disclosure. Typically, such compositions can be prepared as for a typical blood transfusion, either as liquid solutions or suspensions.

The techniques of preparation are generally well known in the art as exemplified by Remington's Pharmaceutical Sciences, 16th Ed. Mack Publishing Company, 1980, or most recent edition, incorporated herein by reference. Moreover, for human administration, preparations should meet sterility, pyrogenicity, general safety and purity standards as required by the U.S. Food and Drug Administration. Upon formulation, the therapeutic compositions are administered in a manner compatible with the dosage formulation and in such amount as is therapeutically effective.

Administration

Suitable methodology for administration of sickle erythrocytes, erythroblasts, sickle variants of the claimed invention is parenteral infusion or injection in a manner similar to a conventional blood transfusion with delivery between 5-500 ml of sickle cells/hr via a secure intravenous or intraarterial catheter.

Dosage

An effective dose of sickle erythrocytes is administered to a subject in need thereof. A "therapeutically effective amount" is an amount of the therapeutic composition sufficient to produce an anti-tumor response when combined with a VDA and radiation therapy. An anti-tumor effect is indicated by a reduction of tumor volume by 25-50% or production of stable tumor size for 2 months. Histopathologically, an anti-tumor effect is associated with tumor infarction due to sickle cell vaso-occlusion in tumor blood vessels. Metes and bounds of transfusion volumes are from 10 ml to 500 ml of sickle cells or sickle variant cells administered intravenously every 2-10 days for up to 3 weeks. The treatment is preferably given in combination with radiation and combretastatin or combretastatin prodrug.

In a preferred schedule the sickle cell infusion is administered 4-48 hours after radiation treatment at about the same time as combretastatin or combretastatin prodrug treatment. Actual dosage levels of active ingredients in the pharmaceutical compositions of the claimed compositions can be varied at the discretion of the health care provider in order to administer an amount that is effective to achieve the desired therapeutic response.

The potency of a therapeutic composition can vary, and therefore a "therapeutically effective" amount can vary. However, using the assay methods described herein below, one skilled in the art can readily assess the potency and efficacy of a composition of this presently claimed subject matter and adjust the therapeutic regimen accordingly.

One of ordinary skill in the art can tailor the dosages to an individual patient, taking into account the particular formulation, method of administration to be used with the composition, and tumor size considering patient height and weight, severity and stage of symptoms, and the presence of additional deleterious physical conditions. Such adjustments or variations as well as evaluation of when and how to make such adjustments or variations are well known to those of ordinary skill.

Toxicity is assessed using criteria set forth by the National Cancer Institute and is reasonably defined as any grade 4 toxicity or any grade 3 toxicity persisting more than 1 week. Dose is also modified to maximize anti-tumor or anti-angiogenic activity.

Methods of Administration of Combretastatin and Combretastatin Prodrugs

As explained above, the present invention is directed towards methods for modulating tumor growth and metastasis comprising, interalia, the administration of a VDA and sickle cells. The agents of the invention can be administered separately (e.g. formulated and administered separately), or in combination as a pharmaceutical composition of the present invention. Administration can be achieved by any suitable route. Such as parenterally, transmucosally, e.g., orally, nasally, or rectally, or transdermally. Preferably, administration is parenteral, e.g., via intravenous injection or infusion. Alternative means of administration also include, but are not limited to, intra-arteriole, intramuscular, intradermal, subcutaneous, intraperitoneal, intraventricular, and intracranial administration/or by injection into the tumor(s) being treated or into tissues Surrounding the tumor(s).

The pharmaceutical composition may be employed in any suitable pharmaceutical formulation, as described above, including in a vesicle. Such as a liposome see Langer, Science 249:1527-1533 (1990); Treat et al., in Liposomes in the Therapy of Infectious Disease and Cancer, Lopez-Berestein and Fidler (eds.), Liss: New York, pp. 317-327, see generally, ibid. Preferably, administration of liposomes containing the agents of the invention is parenteral, e.g., via intravenous injection, but also may include, without limitation, intra-arteriole, intramuscular, intradermal, subcutaneous, intraperitoneal, intraventricular, and intracranial administration, or by injection into the tumor(s) being treated or into tissues Surrounding the tumor(s).

In yet another embodiment, the VDA composition of the present invention can be delivered in a controlled release system, such as using an intravenous infusion, an implantable osmotic pump, a transdermal patch, liposomes, or other modes of administration. In a particular embodiment, a pump may be used see Langer, supra; Sefton, CRC Crit. Ref Biomed. Eng. 14:201 (1987); Buchwald et al., Surgery 88:507 (1980); Saudek et al., N. Engl. J. Med. 321: 574 (1989). In another embodiment, polymeric materials can be used see Medical Applications of Controlled Release, Langer and Wise (eds.)/CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. 23:61 (1983); see also Levy et al., Science 228: 190 (1985): During et al., Ann. Neurol. 25:351 (1989); Howard et al., J. Neurosurg, 71:105 (1989). In yet another embodiment, a controlled release system can be placed in proximity of the target tissues of the animal, thus requiring only a fraction of the systemic dose see, e.g., Goodson, in Medical Applications of Controlled Release, supra, Vol. 2, pp. 115-138 (1984).). In particular, a controlled release device can be introduced into an animal in proximity of the site of inappropriate immune activation or a tumor. Other controlled release systems are discussed in the review by Langer Science 249:1527-1533 (1990).

Controlled release formulation can be pulsed, delayed, extended, slow, steady, immediate, rapid, fast, etc. It can comprise one or more release formulations, e.g. extended- and immediate-release components. Extended delivery systems can be utilized to achieve a dosing internal of once every 24 hours, once every 12 hours, once every 8 hours, once every 6 hours, etc. The dosage form/delivery system can be a tablet, or a capsule suited for extended release, but a sustained release liquid or suspension can also be used. A controlled release pharmaceutical formulation can be produced which maintains the release of, and or peak blood plasma levels of a compound of the invention.

The VDA may also be administrated transdermally using methods known to those skilled in the art (see, for example: Chien: "Transdermal Controlled Systemic Medications': Marcel Dekker, Inc. 1987; Lipp et al. WO94/041573 March 1994). For example, a solution or suspension of a compound of the invention in a Suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or Suspension of a compound of the invention may be formulated into a lotion or salve.

Suitable solvents for processing transdermal delivery systems are known to those skilled in the art, and include lower alcohols such as ethanol or isopropyl alcohol, lower ketones Such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents may also include mixtures of one or more materials selected from lower alcohols, lower ketones, lower carboxylic acid esters, polar ethers, lower hydrocarbons, halogenated hydrocarbons.

Suitable penetration enhancing materials for transdermal delivery system are known to those skilled in the art, and include, for example, monohydroxy or polyhydroxy alcohols such as ethanol, propylene glycol or benzyl alcohol, saturated or unsaturated C8-C18 fatty alcohols such as lauryl alcohol or cetyl alcohol, saturated or unsaturated C8-C18 fatty acids such as stearic acid, saturated or unsaturated fatty esters with up to 24 carbons such as methyl, ethyl, propyl, isopropyl. n-butyl, sec-butyl, isobutyl, tertbutyl ormonoglycerinesters of acetic acid, caprinic acid, lauric acid, myristinic acid, stearic acid, or palmitic acid, or diesters of saturated or unsaturated dicarboxylic acids with a total of up to 24 carbons Such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations may also include mixtures of one or more materials selected from monohydroxy or polyhydroxy alcohols, saturated or unsaturated C8-C18 fatty alcohols, saturated or unsaturated 08-C18 fatty acids, saturated or unsaturated fatty esters with up to 24 carbons, diesters of Saturated or unsaturated discarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrenebutadiene copolymers, and natural and synthetic rubbers. Cellulose ethers, derivatized polyethylenes, and silicates may also be used as matrix components. Additional additives. such as viscous resins or oils may be added to increase the viscosity of the matrix.

Pharmaceutical compositions employed in the methods of the invention include a VDA formulated with other ingredients, e.g., pharmaceutically acceptable carriers. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans. The term "carrier refers, for example to a diluent, adjuvant, excipient, auxiliary agent or vehicle with which an active agent of the present invention is administered. Such pharmaceutical carriers can be sterile liquids, such as water and oils, including those of petroleum, animal, vegetable or synthetic origin, Such as peanut oil, soybean oil, mineral oil, sesame oil and the like. Water or aqueous saline solutions and aqueous dextrose and glycerol solutions are preferably employed as carriers, particularly for injectable solutions. Other pharmaceutical carriers include, but are not limited to, antioxidants, preservatives, dyes, tablet-coating compositions, plasticizers, inert carriers, excipients, polymers, coating materials, osmotic barriers, devices and agents which slow or retard solubility, etc. Nontoxic pharmaceutically acceptable excipients that are suitable for the manufacture of tablets include, for example, inert diluents, such as calcium carbonate, sodium carbonate, lactose, calcium phosphate or sodium phosphate; granulating and disintegrating agents, for example, corn oil, corn starch, or alginic acid; and binding agents, for example magnesium stearate, stearic acid or talc. Suitable pharmaceutical carriers are described in "Remington's Pharmaceutical Sciences" by E. W. Martin. A pharmaceutical composition of the present invention can be administered by any suitable route, for example, by injection, by oral, pulmonary, nasal or other forms of administration. In general, pharmaceutical compositions contemplated to be within the scope of the invention, comprise, inter alia, pharmaceutically acceptable diluents, preservatives, solubilizers, emulsifiers, adjuvants and/or carriers. Such compositions can include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc., or into liposomes. Such compositions may influence the physical state, stability, rate of in vivo release, and rate of in vivo clearance of components of a pharmaceutical composition of the present invention. See, e.g., Remington's Pharmaceutical Sciences, 18th Ed. (1990, Mack Publishing Co., Easton, Pa. 18042) pages 1435-1712 which are herein incorporated by reference. A pharmaceutical composition of the present invention can be prepared, for example, in liquid form, or can be in dried powder such as lyophilized form. Particular methods of administering such compositions are described infra.

Aqueous suspensions containing the active materials in admixture with excipients suitable for the manufacture of aqueous Suspensions may also be used. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents may be a naturally occurring phosphatide, for example, lecithin, or condensation products of an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl hydroxybenzoate, one or more coloring agents, one or more flavoring agents, and one or more sweetening agents such as sucrose or saccharin.

Preferred Dosage Ranges Combretastatin and Combretastatin Prodrug Therapy

These dosages provide guidance in selecting dosages for combretastatins and combretastatin prodrugs. In one exemplary embodiment, a suitable dose per day for VDA (e.g. a combretastatin or combretastatin prodrug), can be, individually, in the range of from about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg. about 400 ng to about 4,500 mg, about 500 ng to about 4,000 mg, about 11 µg to about 3,500 mg, about 5 µg to about 3,000 mg, about 10 µg to about 2,600 mg, about 201 g to about 2.575 mg, about 30 ug to about 2.550 mg, about 40 µg to about 2,500 mg, about 50 g to about 2.475 mg, about 100 ug to about 2.450 mg, about 200 µg to about 2,425 mg, about 300 lug to about 2,000, about 400 µg to about 1,175 mg, about 500 µg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg. or about 525 mg to about 625 mg.

Other suitable doses for the VDA include, for example, 0.1 mg/kg to about 100 mg/kg, from about 1 mg/kg to about 100 mg/kg, from about 5 mg/kg to about 50 mg/kg, from about 10 to about 25 mg/kg: about 10 mg/kg; about 15 mg/kg, about 20 mg/kg, about 25 mg/kg, about 30 mg/kg; about 40 mg/kg, about 50 mg/kg: about 60 mg/kg; about 70 mg/kg; about 80 mg/kg; about 90 mg/kg, and about 100 mg/kg. In a preferred embodiment, the VDA (e.g., a combretastatin or flavinoid agent) is administered at a dose ranging from between 45 mg/kg and 63 mg/kg.

Tumors to Treat

In particularly preferred embodiments, the methods of the invention are used to treat solid tumors. As is well known in the art, solid tumors are quite distinct from nonsolid tumors such as those found in hemopoietic-related cancers. A solid tumor can be malignant, e.g. tending to metastasize and being life threatening, or benign. Examples of solid tumors that can be treated or prevented according to a method of the present invention include sarcomas and carcinomas Such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, gastric cancer, pancreatic cancer, breast cancer, ovarian cancer, fallopian tube cancer, primary carcinoma of the peritoneum, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, liver metastases, bile duct carcinoma, choriocarcinoma, seminoma, embryonal carcinoma, thyroid carcinoma such as anaplastic thyroid cancer, Wilms tumor, cervical cancer, testicular tumor, lung carcinoma such as small cell lung carcinoma and non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

The following methods and examples provide practical evidence of the workability of the instant invention. The ability of sickle cells with CA-4, (AVE8062, ombrabulin) or CAP (Oxi4503) plus radiation to induce a tumoricidal response, comprehensive tumor necrosis and complete tumor regressions is shown in examples 1-8. The chain of events leading to complete tumor regression using these tool is shown in Example 11.

Materials and Methods

Mice

Male and female mice 8-12 weeks of age weighing 19-26 grams were used. C57BL/6J, hemoglobin S knock-in mice (SSKI) (B6; 129-Hbat$^{tm1(HBA/Tow}$ Hbb$^{tm2(HBG1,HBB*/Tow}$/J) and homozygous hemoglobin A knock-in mice (AAKI) (B6; 129-Hba$^{tm1(HBA/Tow}$ Hbb$^{tm3(HBG1,HBB)Tow}$/J) were obtained from a breeding colony maintained at UAB animal research facility. QTL evaluation of SSKI and AAKI mice indicated that they are predominantly B6 and exhibit up to 30% of 129 genes. The animals were housed 7 animals per cage in a 12-hour light-dark cycle with water, food ad libitum.

Tumor Cell Lines and Pharmaceuticals

The Lewis lung carcinoma (LLC) were obtained from ATCC (Manassas, Va.). CA-4 (AVE8062) was obtained from Sigma-Aldrich (St. Louis Mo.), CAP (Oxi4503) from Cayman (Ann Arbor Mich.) and 5,6-dimethylxanthenone-4-acetic acid DMXAA Sigma USA. Pimonidazole hydrochloride [1-[(2-hydroxy-3-piperidinyl)propyl]-2-nitroimidazole-hydrochloride] from Hypoxyprobe, Inc. (Burlington, Mass.).). Caki-1 cells were supplied by Dietmar Siemann (Department of Radiation Oncology, University of Florida, Gainesville, Fla.).

Hyperspectral Imaging

In vivo hyperspectral imaging experiments with mouse window chamber tumors were conducted in accordance with a protocol approved by the University of Florida Institutional Animal Care and Use Committee. Hemoglobin saturation determinations in the tumor microvasculature using hyperspectral imaging information was described previously (Sorg B S, J Biomed Opt. 2005; 10(4):44004). A Zeiss Axioskop 2 microscope (Carl Zeiss, Inc., Thornwood, N.Y.) served as the imaging platform. Images were acquired with a CCD camera (DVC Company, Austin, Tex.), and bandlimited optical filtering for hyperspectral imaging was accomplished with a C-mounted liquid crystal tunable filter (CRI, Inc., Woburn, Mass.). Image processing was performed using Matlab software (The Mathworks, Inc., Natick, Mass.). Microvessel-based pixel counts of vessels in window chamber tumors were quantitated as a fraction of microvessels pixels over the total number of micropixels in the tumor.

Collection, Preparation and Treatment of Human and Mouse RBCs

Normal RBCs were obtained from normal healthy adults and SSRBCs from patients with homozygous sickle cell anemia. Fresh blood samples were collected into citrate tubes. RBCs were separated from the buffy coat by gravity at 4° C. for at least 2 hours. Plasma and buffy coat were removed by aspiration and RBCs were washed four times in sterile PBS with 1.26 mM $Ca^{2+}$, 0.9 mM $Mg^{2+}$ (pH 7.4). SSRBCs or HbA RBCs (AARBCs) were obtained from SS knockin (SSKI) or AA knockin (AAKI) mice by cardiac puncture into EDTA coated tubes. RBCs were separated and washed as described above. The cells were diluted to Hct 50% in PBS and administered intravenously via the retro-orbital vein.

Radiation

Radiation was carried out using a X-RAD 320 irradiator (Precision X-Ray). Mice were anesthetized with 1.6% Avertin in PBS (Sigma Aldrich T48402-5G) and positioned in a metal jig exposing the tumor while shielding the body. In all studies where radiation was used it was delivered to tumor as a single dose of 10 Gy at 1 Gy/minute.

Tumor Therapy with Combretastatin A4, SSRBCs and Radiation

Mice were injected in the right flank with $10^3$ LLC cells in volume of 50 μL containing 25 μL of Matrigel (Fisher Scientific). Tumor volumes were measured daily with standard calipers and volumes were calculated as length× width$^2$/2 where length is the long axis and width the short axis. The endpoint was a tumor volume of 750-1500 mm$^3$. Lyophilized CA-4 was hydrated in sterile distilled water under dark conditions. In vivo studies were started when tumors reached a median diameter of 78 mm$^3$ (53-94 mm). In the passive transfer protocol, tumors were radiated with 10 Gy on day 12. On day 13, CA-4 30 mg/kg in 50 μL of sterile distilled water was administered intraperitoneally (ip) followed by intravenous delivery of human or mouse SSRBCs or AARBCs from HbS sickle cell knockin mice or HbA knockin mice respectively in 200 μL of PBS, hematocrit 50%. CA-4 and SSRBCs or AARBC treatment was repeated on days 15 and 18. Tumors were measured daily with Vernier calipers. Mice were euthanized if toxicity was evident or tumor burden exceeded 500 mm$^3$. In the SSKI treatment protocol, tumors established in SSKI or AAKI mice were radiated with 10 Gy on day 12 as described above and treated with CA-4 30 mg/kg ip on days 13, 15 and 18. Histologic and immunohistochemical samples were obtained on day 22 in the passive transfer study and on day 20 in the SSKI protocol.

Tumor Therapy with Oxi4503, SSRBCs and Radiation

LLC tumor cells ($10^5$ were implanted subcutaneously on day 0. On day 12, when tumor reached a diameter of at least 0.5 mm³ they were radiated with 10 Gy. On day 13, Oxi4503 (Cayman, Ann Arbor Mich.) 10 mg/kg in 50 µL of PBS or DMXAA (Sigma USA) 18 mg/kg was administered intraperitoneally (ip) followed by intravenous delivery of mouse. SSRBCs from HbS sickle cell knockin mice in 200 µL of PBS, hematocrit 50%. This regimen was repeated on days 21 and 22.

Methionine Depletion with Diet and FIDAS-5

LLC tumor cells ($10^5$ were implanted subcutaneously on day 0. On day 12, when tumor reached a diameter of at least 0.5 mm³ they were radiated with 10 Gy. On day 13, Oxi4503 10 mg/kg in 50 µL of PBS was administered intraperitoneally (ip) followed by intravenous delivery of mouse SSRBCs from HbS sickle cell knockin mice in 200 µL of PBS, hematocrit 50%. Beginning on day 12, mice were begun on a methionine deficient diet (Dyets, Bethlehem Pa.) as described in detail above. They were also treated with FIDAS-5 (Sigma-Aldrich) 40 mg/kg ip on days 14-29. The addition of methionine deficiency to the Oxi4905/SSRBCs/rad regimen was compared to that of individual groups treated with anti-IL-4 (500 µg ip on days 14,17,20), anti-IL-25 (500 µg ip on day 10), anti-IL-10 (250 µg ip on days 14,17,20) and Toll 9 receptor oligonucleotide inhibitor (25 µg ip on day 13) together with the said Oxi4905/SSRBCs/rad regimen.

Pimonidazole Uptake in Tumors

Pimonidazole at doses of 60 mg/kg body weight in 1 ml 0.9% normal saline was administered iv to the tumor-bearing mouse. Tumors are harvested 60 minutes after Hypoxyprobe™-1 administration. The tumors were dissected and fixed in phosphate-buffered 4% paraformaldehyde and embedded in paraffin casts before 5-µm histological sections were cut.

Histology and Immunohistochemistry

Mice were anesthetized with ketamine and tumors were excised surgically. The tumors were fixed with formalin and embedded in paraffin. Serial sections 5 µm thick were cut from the formalin fixed, paraffin embedded tissue blocks and floated onto charged glass slides (Super-Frost Plus, Fisher Scientific, Pittsburgh, Pa.) and dried overnight at 60° C. Sections were stained with hematoxylin-eosin (H&E). For immunohistochemical staining, tumor sections were deparaffinized and hydrated using graded concentration ratios of ethanol to deionized water. The sections were then incubated with 0.01M Tris-1 mM EDTA buffer (pH 9) in a pressure cooker for 5 min. Sections were then washed in deionized water and transferred to 0.05 M Tris-based solution in 0.15M NaCl with 0.1% v/v Triton-X-100, pH 7.6 (TBST). Endogenous peroxidase was blocked with 3% hydrogen peroxide for 10 min. To reduce further nonspecific background staining, slides were incubated with 3% normal goat serum (Sigma, St Louis, Mo.) for 30 min at room temperature. Slides then were incubated overnight at 4° C. with rabbit anti-mouse Ki67 monoclonal antibody at 1:50 dilution (Thermo Fisher, RM-9106-S0) or mouse anti-pimonidazole IgG1 monoclonal antibody at 1:50 dilution (Hypoxyprobe, Burlington, Mass.). Negative controls were produced by eliminating the primary antibodies from the diluents. After washing with TBST, sections treated with anti-Ki67 or anti-pimidazole were incubated with 1:1000 dilution of goat anti-rabbit IgG H&L (HRP) (Abcam, ab6721) or 1:100 dilution of goat anti-mouse IgG H&L (HRP) (Abcam, ab6789) respectively. Diaminobenzidine (DAB; Scy Tek Laboratories, Logan, Utah) was used as the chromagen and hematoxylin (no. 7211, Richard-Allen Scientific, Kalamazoo, Mich.) as the counterstain.

Histochemical Quantitation of Residual Viable Tumor, Fraction of Hypoxic Cells, Tumor Vaso-Occlusion and Ki-67 Positive Cells Histochemical quantitation of Ki-67 immunopositive cells was carried out at ×40 magnification on 30 separate fields of tumor and examined using a Leitz Diaplan microscope. The total number of Ki67 immunopositive cells was determined. The area showing pimidazole staining was determined by using the Image-J software (NIH, Bethesda, Md.). The analyses were performed using a magnification of ×10. Values of the fractional area of pimidazole positivity were computed as a function of the total tumor area. Fraction of immunohistochemically hypoxic cells (IHF) was calculated as: $IHF = AF_{pim}/A_{total}$ where $AF_{pim}$ is the fraction showing pimonidazole staining and $A_{total}$ is the total tumor area. Quantitation of vaso-occlusion in tumors was carried out by enumerating the total number of occluded microvessels in 40 fields of H&E-stained tumor sections at ×40 magnification. Microvessels were occluded when at least 80% of the vessel lumen was filled with erythrocytes. Residual viable tumor area was determined on slides of sections from 3-4 treated tumors stained within each group. The H&E stained slides were scanned at 1200 dpi and photographed as a TIFF image. The necrotic and viable area of these sections were identified histologically and corroborated using Image-J software (NIH, Bethesda, Md.). Residual viable tumor area was expressed as the percentage of pixels in the total area minus the area of the necrotic regions in the entire tumor section. Statistical analysis was based on a mean of three to four tumors per group.

Methionine Depletion Diet, FIDAS-5 and Immunotherapeutics

A diet depleted of methionine was obtained from Dyets, Bethlehem Pa. The composition of the diet is shown herein. The S-adenosylmethionine (SAM) inhibitor FIDAS-5 (Sigma, USA) was used to ensure comprehensive intracellular methionine depletion. FIDAS-5 20 mg/kg was dissolved in corn oil and delivered in volume a volume of 50 µL ip. Mouse anti-CD25 antibody, clone PC61 and anti-mouse IL-4 antibody, clone 11B11 were obtained from Biolegend, USA. Mouse anti-IL-10 antibody was obtained from BioXcell USA Toll 9 antagonist ODN 2088 was obtained from InvivoGen USA. Dosages of immunotherapeutics are provided in the Results section.

Statistical Analyses.

For comparison of individual data points, two-tailed Student's t-test was applied to determine statistical significance along with ANOVA one-way analysis of variance with Bonferroni's adjustment. $p = <0.05$ values were considered statistically significant and $p<0.01$ values were considered highly statistically significant. Data were analyzed by 2-tailed Student's t test, and $p<0.05$ was considered statistically significant.

EXAMPLES

Example 1: Assessment of VDA Ability to Induce Hypoxia in Caki-1 and Lewis Lung Tumors Using hyperspectral imaging we assessed the spatial and kinetic effects of CA-4 on the development and recovery of tumor hypoxia, vascular collapse and parenchymal injury in the Caki-1 tumor. In FIG. 1, representative of two experiments, hyperspectral imaging of the untreated Caki-1 tumor displayed an area of 38% with a Hb saturation of <10% (FIG. 1A,D,G) Four hours after treatment with CA-4, 63% of the tumor area exhibited <10% Hb saturation while light field microscopy showed collapse of tumor microvessels at the tumor core (p=<0.000002, FIG. 1 B, E, G). At 48 hours brightfield observations revealed obliteration of tumor vessels in the tumor core while hyperspectral imaging showed partial recovery of oxygenation in the tumor periphery (FIG. 1, C,F,G). From these observations, we postulated that tumor microvascular hypoxia (Hb sat<10%) and vessel collapse of this order induced by CA-4 within 4 hours after administration would enable SSRBCs to deoxygenate and their HbS to polymerize as shown in vitro (Noguchi C T *Proc Natl Acad Sci USA*. 1980; 77(9):5487-5491). Under these conditions SSRBCs also assume the sickle morphology and upregulate intrinsic adhesion receptors resulting in SSRBC aggregation and vaso-occlusion. The narrow time dependency for induction of tumor vascular hypoxia and vessel and collapse by these agents indicated that to optimize the vaso-occlusive effect of SSRBCs both SSRBCs and CA-4 would need to be administered at the same time.

Example 2: Transfused Sickle Cells Induce a Vaso-Occlusive Surge in Response to CA-4 and Sublethal Radiation Resulting in Broadly Propagated Tumor Hypoxia and Infarction Engulfing the Core and Treatment-Resistant Tumor Rim Because of their biocompatibility with humanized sickle cell knockin (SSKI) mice we carried out additional studies of tumor hypoxia with CA-4 alone and combined with SSRBCs and sublethal radiation (SR) using the venerable pimidazole hypoxia marker in C57BL/6 mice bearing established Lewis lung carcinoma (LLC) (FIG. 2 A-C). Intracellular pimidazole is activated in vivo by deoxygenation in a range of 0-10% mm Hg similar to that noted after CA-4 administration to the Caki-1 tumors (Rofstad E K, *Int J Radiat Biol*. 1999; 75(11):1377-1393).

Next, we determined whether SSRBCs transfusion together with CA-4 could induce vaso-occlusion and hypoxia in the microvessels of established LLC. The LLC tumor in C57B/6 mice was selected for its biocompatibility with humanized sickle cell knockin mice whose SSRBCs would be used for the transfusion. These strains share a common background and reject the LLC in a similar fashion. Mice with established LLC were treated with CA-4, alone or together with infusion of SSRBCs obtained from humanized HbS sickle cell knockin (SSKI) mice and sacrificed 24 hours later. Analysis of tumor sections showed a modest degree of vaso-occlusion and pimidazole-reactive hypoxic cells in the treated groups (FIG. 2C). We next examined the effect of sublethal radiation (SR) to the tumor alone or together with CA-4 or SSRBCs on tumor vaso-occlusion and hypoxia. We reasoned that since tumor SR induces mitotically-based and ROS-driven tumor endothelial apoptosis it could augment the vascular injury, tumor hypoxia and vaso-occlusion induced by CA-4 and SSRBCs (Garcia-Barros M, et al. *Science*. 2003; 300(5622):1155-1159). After the addition of tumor SR to CA-4 we observed a significant increase in pimidazole reactive tumor cells encompassing 40% of the tumor area (FIG. 2C). We therefore combined tumor SR and CA-4 with SSRBC infusions. Mice with established tumors were treated with sublethal radiation to the tumor and 24 hours later received CA-4 together with infusion of SSRBCs. Surprisingly, tumor sections obtained 24 hours after concluding treatment showed massive tumor microvessel closure and associated infarction that engulfed the core and the treatment-resistant tumor rim (FIG. 3 A-E). Simultaneously, the SSRBC-based triple therapy significantly increased the tumor hypoxic fraction and limited the number of proliferating Ki67+ tumor cells (FIGS. 2C, 4 A-C). Mice similarly treated with AARBCs obtained from humanized HbA knockin mice (AAKI) showed a significantly lower degree of tumor vaso-occlusion, hypoxia and infarction than SSKI mice; mice treated with single or dual modalities showed minimal vaso-occlusion, infarction and hypoxia (FIGS. 2D, 3E). These results indicate that SSRBCs work synergistically with CA-4 and tumor SR to broadly propagate tumor vaso-occlusion, hypoxia and infarction. Importantly, the massive infarctions induced by SSRBC-based triple therapy obliterated pimidazole-positive pockets and the treatment-resistant tumor rim (FIGS. 2C, 3 A-E). CA-4 together with tumor SR were more effective in inducing tumor hypoxia (FIG. 2C) than either one alone suggesting that cumulative tumor microvessel conditioning/injury induced by these modalities unleashes a robust SSRBC-mediated vaso-occlusive and tumoricidal response.

Example 3: Repeated Sickle Cell Infusions Induce Regression of Established LLC when Combined with CA-4 and Sublethal Radiation (SR)

Having shown that SSRBC infusions together with CA-4 and tumor SR could produce disseminated tumor vaso-occlusion, hypoxia and infarction encompassing the tumor rim we next determined whether repeated treatment of established lung tumors with the triple modality regimen could induce significant tumor regressions. Mice with established Lewis lung tumors were treated with SR to the tumor on day 12 and 24 hours later (day 13) received CA-4 along with infusions of SSRBCs obtained from SSKI mice or humans with sickle cell anemia. SSRBC infusion and CA-4 were repeated on days 15 and 18 and mice were sacrificed on day 22. Results showed that mouse or human SSRBCs coupled with CA-4 and SR produced significant arrest of LLC growth on day 22 (FIG. 5A). By contrast, mice similarly treated with RBCs from AAKI mice or a normal human donor showed tumor progression (FIG. 5A). Combining SSRBCs infusions with CA-4 or tumor SR individually or administering CA-4 together with tumor SR without SSRBCs infusions produced LLC progression (FIG. 5A). Analysis of tumor sections from mice passively infused with mouse or human SSRBCs plus CA-4 and SR on day 22 showed extensive tumor vaso-occlusion and infarction enveloping the core and tumor periphery (FIG. 5 B,C). In the SSRBC-based triple therapy group residual viable tumor area was confined to less than 5% of the tumor area providing histologic corroboration for the observed tumor regressions (FIG. 6). This reduction in residual viable tumor area was significantly lower than in mice similarly treated with mouse or human AARBCs and controls receiving single or dual agents (FIG. 6). Collectively, these data demonstrate the ability of passively infused SSRBCs to induce tumor regressions in vivo when combined with CA-4 and tumor SR. They further underscore the primacy of SSRBCs over AARBCs in the tumoricidal process.

Example 4: Sickle Cell Knockin (SSKI) but not HbA Knockin (AAKI) Mice Treated with CA-4 and Sublethal Radiation Exhibit Tumor Regressions Affirming the Primacy of SSRBCs in the Tumoricidal Response In Vivo Having shown that passive infusions of SSRBCs but not AARBCs induced tumor regression in mice in combination with CA-4 and tumor SR, we hypothesized that repeated treatment of SSKI but not AAKI mice would recapitulate the tumoricidal response. SSKI or AAKI mice with established lung tumors were treated with SR on day 12 followed by CA-4 on 15 days 13, 15 and 18. Treatment with tumor SR or CA-4 individually failed to retard LLC growth (FIG. 7A). By contrast, treatment of SSKI mice but not AAKI mice with tumor SR plus CA-4 ×3 completely abolished LLC growth (FIG. 7A). Analysis of tumor sections from SSKI mice treated with CA-4 and tumor SR showed broadly propagated tumor infarctions engulfing the core and tumor periphery associated with tumor cell necrosis, mononuclear cell infiltration and a significantly greater number of occluded microvessels and smaller area of residual viable tumor than similarly treated AAKI mice (FIGS. 7B,C,D; FIG. 8A,B). The SSRBC-mediated vessel occlusions were often clustered and tightly packed with erythrocytes of which nearly 100% exhibited a sickle cell morphology (FIG. 7C). Since only 5% of circulating non-deformable sickle cells in SSKI mice display the sickle morphology it is likely that SSRBCs trapped in the injured tumor microvessels transitioned to the sickle shape as their HbS deoxygenated and polymerized. That therapy with SR and CA-4 in SSKI but not AAKI mice can induce tumor regression in vivo these findings confirm the key role of SSRBCs in the vaso-occlusive tumoricidal process. They show for the first time a powerful synergy between these tools resulting in a sharp surge of tumor vaso-occlusion and infarction, comprehensive in scale that eradicates the core and treatment-resistant tumor rim with consequent tumor regression.

Example 5. Repeated Sickle Cell Infusions Combined with Oxi4503 and Sublethal Radiation (SR) is Superior to Sickle Cell Infusion Combined with DMXAA and SR in Inducing Extended Tumor Regression of Established LLC LLC tumor cells ($10^5$ were implanted subcutaneously on day 0. On day 12, when tumor reached a diameter of at least 0.5 $mm^3$ they were radiated with 10 Gy. On day 13, Oxi4503 (10 mg/kg in 50 μL of PBS) or DMXAA (18 mg/kg) were administered intraperitoneally (ip) followed by intravenous delivery of mouse. SSRBCs from HbS sickle cell knockin mice in 200 μL of PBS, hematocrit 50%. This regimen was repeated on days 21 and 22. FIG. 9 shows that (A) Oxi4503 combined with SSRBCs and radiation was effective in inducing tumor grow delay. Two cycles of the SSRBCs/Oxi4503/radiation produced complete tumor growth retardation and was superior to a single cycle (p=0.001). In addition, the Oxi4503/SSRBCs/radiation regimen was superior to the DMXAA/SSRBCs/radiation in inducing tumor growth impairment (p<0.001). (B) (B) Section from mouse bearing established LLC on day 14 after treatment with radiation 10 Gy on day 12 followed by infusion of SSRBCs and Oxi4503 on day 13 shows disseminated tumor vaso-occlusion with erythrocytes displaying the sickle cell morphology trapped in occluded vessels. This associated with broadly propagated tumor infarction and tumor cell necrosis (H&E ×10 and ×25 magnification).

Example 6. Sickle Cell Infusion Combined with CA-4 and Sublethal Radiation (SR) Induces Extended Tumor Regression of Established LLC when Coupled with Methionine Depletion and FIDAS-5

LLC tumor cells (10 were implanted subcutaneously on day 0. On day 12, when tumors reached a diameter of at least 0.5 cm in diameter they were radiated with 10 Gy. On day 13, Oxi4503 (10 mg/kg in 50 μL of PBS) was administered intraperitoneally (ip) followed by intravenous delivery of mouse SSRBCs from HbS sickle cell knockin mice in 200 μL of PBS, hematocrit 50%. Beginning on day 12, mice were begun on a methionine deficient diet (Dyets, Bethlehem Pa.) as described in detail above. They were also treated with FIDAS-5 (Sigma-Aldrich) 40 mg/kg ip on days 14-29. To compare the addition of methionine deficiency to the Rad/Oxi4503/SSRBCs regimen we introduced immunotherapeutic agents together with the latter treatment. Radiation, Oxi4503 and SSRBCs were administered on days 12 and 13 as described above. In group, mouse anti-CD25 500 μg was delivered ip on day 10. In group 2, mouse anti-IL-4 was administered ip on days 14,17,20. In group 3, mouse anti-IL10R was delivered ip on days 14,17,20. Toll 9 oligonucleotide antagonist ODN288 (10 mg/kg) was given ip on day 13. Results shown in FIG. 10 indicate that Rad/Oxi4503/SSRBCs combined with methionine depletion regimen this regimen induced complete tumor growth arrest by day 30. This regimen was also superior to Rad/Oxi4503/SSRBCs combined with immunotherapeutic drugs anti-IL-4, anti-IL10 and anti-CD25 or ODN288 in producing tumor growth retardation (p=0.003 relative to anti-IL-4; p<0.0001 for all other treatments (FIG. 10).

Example 7: Toxicity of Treatments

The treatments were well tolerated at the specified doses. Histologic analysis of heart, lungs, kidneys, liver of SSKI mice treated with CA-4 and radiation treated tumor bearing SSKI mice or similarly treated tumor bearing C57BL/6 mice passively infused with SSRBCs showed no evident vaso-occlusion, thrombosis, infarction or hemorrhage. Spleens from treated C57BL/6 mice showed no changes from the untreated mice. Compared C57BL/6 mice, spleens from untreated SSKI mice were significantly enlarged and red pulp sinusoids were congested with sickle cells with no evidence of old or acute infarctions. Relative to spleens from untreated SSKI mice, spleens from treated SSKI mice showed slightly more sinusoidal congestion but no evident vaso-occlusion, fresh infarction or hemorrhage.

Example 8: Scheme of the Chain of Events Leading to Complete Tumor Regressions Following Treatment with Sickle Cells, Ombrabulin, and Radiation. See FIG. 11

Discussion

Here we introduce hypoxia-reactive SSRBCs as a new therapeutic that unleashes massive tumor vaso-occlusion and infarction in the presence of tumor endothelial injury and hypoxia induced by CA-4 and SR. The dynamic chain of events culminates in comprehensive eradication of established tumors engulfing treatment resistant hypoxic niches and the tumor rim. The treatment effect was selective for tumors and correlated with a major pathologic response predictive of prolonged survival in lung cancer patients (Hellmann M D, et al *Lancet Oncol.* 2014; 15(1):e42-e50). SSRBCs were requisite for the tumoricidal response since the anti-tumor effect occurred in humanized SSKI mice but not in similarly treated AAKI mice. SSRBCs therefore emerge as an indispensable and paramount effector in the profound tumoricidal synergy with CA4 and SR.

The central therapeutic in the tumoricidal effect is the SSRBC which produces broadly propagated tumor vaso-occlusion-infarction in the tumor microvasculature conditioned by CA4-SR-induced hypoxia and vascular injury. In the proposed chain of events (FIG. 9) both SR and CA-4 induce endothelial injury, the former via single and double stranded DNA breaks and the latter by means of endothelial cytoskeletal/microtubule injury following disruption of the VE-cadherin/β-catenin/Akt signaling pathway (Kanthou C, Tozer G M. *Blood.* 2002; 99(6):2060-2069). The resulting endothelial blebbing and rounding up impinges on the microvascular lumen leading to blood stagnation and the observed significant increase in tumor hypoxia (Hori K, Saito S. *Br J Cancer.* 2003; 89(7):1334-1344). In the face of this degree of blood stasis and tumor hypoxia, SSRBC HbS deoxygenates and polymerizes resulting in increased SSRBC rigidity, and blood viscosity. Desaturated SSRBCs trapped in this milieu adhere to vessel walls and form microvascular aggregates to account for broadly propagated vaso-occlusion and the appearance of tightly packed SSRBCs in the occluded tumor vessels. Because only 5% of circulating SSRBCs exhibit the sickle morphology, the appearance of sickled shaped cells in the occluded vessel confirms the key role of drug-induced blood stagnation and hypoxia in the sickle cell transformative process. The disseminated tumor vessel closure explains the surge of pimidazole-positive hypoxic tumor cells and extensive infarction in the tumor parenchyma. The widespread tumor cell death is primarily due to infarction-based oxygen deprivation evidenced by the disseminated hypoxia, infarction, mononuclear cell infiltration, sharp reduction in residual viable tumor cells and mitotically active Ki67 positive cells. Collectively, these finding unveil a hitherto unrecognized synergy between SSRBCs and CA-4-SR wherein CA-4-SR induce severe tumor endothelial cell injury that unleashes a massive adaptative surge of SSRBC remodeling and tumor vaso-occlusion. The resulting extensive tumor infarctions encompass treatment-resistant hypoxic niches and tumor rim leading to regressions in vivo.

In addition to SSRBCs' unique oxygen sensing functionality and proclivity to autoaggregate, their prooxidative membranes and intrinsic heme can also induce ROS-mediated endothelial cell injury (Balla G et al., *Lab Invest.* 1991; 64(5):648-655 Belcher J D et al., *Blood.* 2014; 123(3):377-390). In the absence of such properties inert microparticles and micelles used clinically to induce tumor vessel closure induce no more than 30-60% tumor vaso-occlusion, require loco-regional access for administration and rarely produce complete tumor regression. By contrast, the SSRBC-based regimen shown here administered by non-invasive routes induced comprehensive vaso-occlusion and complete tumor regressions. The scale of the observed tumor cell and stromal eradication likely precludes the emergence of intrinsic growth-promoting hypoxia-inducible factors and alternate angiogenic pathways that have hampered the efficacy of anti-angiogenics. Indeed, the synergistic tumoricidal effect of these agents contrasts sharply with CA-4's ineffectiveness when used alone or together with radiation, conventional anti-angiogenics, biologics or chemotherapy (Garon E B *Onco Targets Ther.* 2016; 9:7275-7283; Nathan P, et al. *Clin Cancer Res.* 2012; 18(12):3428-3439). SSRBCs' vaso-occlusive surge unleashed by CA-4-SR-induced tumor endothelial cell injury, therefore, appears to provide a therapeutic advantage over other combinations.

SR's contribution to the tumor vaso-occlusive effect and infarction when combined with CA-4 and SSRBCs is likely due to cumulative tumor endothelial injury induced by SR's ability to activate endothelial ROS and produce mitotically-based cell death. Tumor cells showing signs of radiation injury were engulfed in the tumoricidal infarction suggesting that radiation-injured tumor cells may be more susceptible to SSRBC-mediated infarction akin to radiated cardiac tissue following induction of experimental myocardial infarction by vascular ligation.

A surprising discovery here is the ability of small amounts of passively infused human or mouse SSRBCs but not AARBC to induce tumor killing in the tumor bearing C57BL/6 mice treated with CA4-SR. This indicates that this treatment is applicable to humans generally and not confined to tumor in subjects with sickle cell anemia. Using a microfluidic flow system, recent studies showed that little as 10% SSRBCs in normal blood samples can significantly alter its viscosity and conductance. This is ascribed to the presence of SSRBCs rendered rigid after multiple cycles of oxygenation-deoxygenation (Lu X, *Biophys J.* 2016; 110 (12):2751-2758). Further studies to phenotype and characterize the conductance of the infused SSRBCs using this and similar integrative techniques will be useful in screening, selecting and standardizing the SSRBC infusate for antitumor activity.

With respect to clinical translation, toxicity, SSRBC infusions in this and previous studies have been delivered safely to more than 100 tumor bearing mice with no significant toxicity. Since SSRBCs largely target hypoxic vasculature with upregulated adhesion receptors, cancer patients with vascular diseases bearing an underlying chronic oxidative stress signature such as hypertension and atherosclerotic cardio- and cerebrovascular disease might be at higher risk of SSRBC treatment. The risk in these settings, however, may be no greater than that of many widely used cancer cytotoxics (e.g., doxorubicin), antiangiogenic agents (e.g., bevacizumab), and biologics (e.g., IL-2), which are known to exacerbate these vascular conditions. The assessment of prospective patients for SSRBC treatment would be similar to that deployed in patients at risk of chemotherapy-associated venous thromboembolism. By excluding those subjects showing an inflammatory and procoagulant phenotype and using small volume SSRBC infusions the risk of SSRBC treatment may be mitigated. Based on the efficacy with low volume passive SSRBCs infusions as described herein we plan to use ABO matched human SSRBCs differentiated from sickle stem/progenitor cells for transfusion into patients with advanced cancer along with parenteral VDA and sublethal tumor radiation.

Finally, we show that CA-4-SR-injured tumor microvessels license SSRBCs to unleash broadly propagated tumor vaso-occlusion and infarction that envelops treatment-resistant tumor niches and produces complete tumor regression. We term this response "induced vaso-occlusive lethality" wherein CA-4-SR is recast in the novel role of remodeling the microvascular environment for a massive surge of SSRBC-driven tumor infarction. These innovative tools strategically deployed thereby constitute a major conceptual advance with compelling translational potential.

What is claimed:

1. A method for treating cancer in a patient, the method comprising: administering an amount of radiation in a first treatment procedure, administering an amount of a combretastatin or combretastatin prodrug in a second treatment procedure and, administering an amount of erythrocytes containing at least one hemoglobin S allele in a third treatment procedure, wherein, the amounts of the first treatment, the second treatment, and third treatment are therapeutically effective in combination.

2. The method according to claim 1, wherein said erythrocytes containing at least one hemoglobin S allele are selected from a group consisting of erythrocytes containing SS hemoglobin, erythrocytes containing SA hemoglobin, erythrocytes containing SC hemoglobin, erythrocytes containing SD hemoglobin, erythrocytes containing SE hemoglobin, erythrocytes containing SAntilles hemoglobin, and erythrocytes containing S beta plus thalassemia hemoglobin.

3. The method according to claim 1, wherein said combretastatin or combretastatin prodrug is delivered parenterally, intravenously by infusion or injection, or intraarterially by infusion or injection, and wherein the delivery may be performed either separately or sequentially with the administration of said erythrocytes containing at least one hemoglobin S allele.

4. The method according to claim 1, wherein said erythrocytes containing at least one hemoglobin S allele in said third treatment is in volume ranging from about 10 ml to 500 ml to the patient is administered.

5. The method according to claim 1, wherein said radiation of the first treatment procedure is administered to the patient in a total dose ranging from about 10 Gy to 60 Gy.

6. The method of claim 1, wherein the said combretastatin prodrug is CA-4 and is administered in a dose range from about 20 mg/m$^2$ to about 70 mg/m$^2$.

7. The method of claim 1, wherein the combretastatin prodrug is CA1P and is administered in a dose range from about 10 mg/kg to about 15 mg/kg.

8. The method according to claim 1, wherein said radiation, combretastatin, or erythrocytes containing at least one hemoglobin S allele are administered simultaneously or sequentially.

9. The method of claim 1, wherein the combretastatin or combretastatin prodrug is administered orally, parenterally, intraperitoneally by injection or infusion, intravenously by injection or infusion, intraarterially by injection or infusion, transdermally, sublingually, intramuscularly by injection or infusion, rectally, transbuccally, intranasally, via inhalation, locally, subcutaneously, intraadiposally by injection or infusion, intraarticularly by injection or infusion or, intrathecally by injection or infusion.

* * * * *